US012760020B2

(12) United States Patent
Katsav et al.

(10) Patent No.: US 12,760,020 B2
(45) Date of Patent: Oct. 13, 2026

(54) SOLID STATE FORMS OF VERICIGUAT AND PROCESS FOR PREPARATION THEREOF

(71) Applicant: ASSIA CHEMICAL INDUSTRIES LTD., Tel Aviv (IL)

(72) Inventors: Luna Ben-Sahel Katsav, Petah Tikva (IL); Jenny Goldshtein, Netanya (IL); Limor Adani, Petah Tikva (IL); Abed Masarwa, Tayibe (IL); Anantha Rajmohan Muthusamy, Sivakasi (IN); Meenakshi Sundaram Somasundaram, Virudu Nagar Dt (IN); Siva Rama Krishna Muppalla, Uttar Pradesh (IN); Anand Kumar Pandey, Uttar Pradesh (IN); Jitendra Kamalakar Sonar, Maharashtra (IN); Sumit Kumar, Yamunanagar (IN)

(73) Assignee: ASSIA CHEMICAL INDUSTRIES LTD., Tel Aviv (IL)

( * ) Notice: Subject to any disclaimer, the term of this patent is extended or adjusted under 35 U.S.C. 154(b) by 318 days.

(21) Appl. No.: 18/683,859

(22) PCT Filed: Aug. 31, 2022

(86) PCT No.: PCT/US2022/042129

§ 371 (c)(1),
(2) Date: Feb. 15, 2024

(87) PCT Pub. No.: WO2023/034364

PCT Pub. Date: Mar. 9, 2023

(65) Prior Publication Data

US 2024/0352014 A1 Oct. 24, 2024

Related U.S. Application Data

(60) Provisional application No. 63/238,842, filed on Aug. 31, 2021.

(30) Foreign Application Priority Data

| | | |
|---|---|---|
| Mar. 30, 2022 | (IN) | 202211018976 |
| Apr. 22, 2022 | (IN) | 202211023924 |
| Jul. 7, 2022 | (IN) | 202211039187 |

(51) Int. Cl.
*C07D 471/04* (2006.01)

(52) U.S. Cl.
CPC .................................. *C07D 471/04* (2013.01)

(58) Field of Classification Search
None
See application file for complete search history.

(56) References Cited

U.S. PATENT DOCUMENTS 8,420,656 B2 4/2013 Follmann et al.
9,604,948 B2 3/2017 Fey et al.

FOREIGN PATENT DOCUMENTS

WO 2011147809 A1 12/2011
WO WO-2013076168 A1 * 5/2013 ........... C07D 471/04

OTHER PUBLICATIONS

International Search Report and Written Opinion of the International Searching Authority issued in corresponding application PCT/US2022/042129 mailed Nov. 9, 2022 (9 pages).

* cited by examiner

*Primary Examiner* — Jeffrey S Lundgren
*Assistant Examiner* — Anthony Joseph Seitz
(74) *Attorney, Agent, or Firm* — Carter, DeLuca & Farrell LLP

(57) ABSTRACT

The present disclosure encompasses solid state forms of Vericiguat, in embodiments crystalline polymorphs of Vericiguat, processes for preparation thereof, and pharmaceutical compositions thereof.

13 Claims, 17 Drawing Sheets

An X-ray Powder Diffractogram (XRPD) of Form V1 of Vericiguat

An X-ray Powder Diffractogram (XRPD) of Form V1 of Vericiguat

An X-ray Powder Diffractogram (XRPD) of Form V2 of Vericiguat

An X-ray Powder Diffractogram (XRPD) of Form V6 of Vericiguat

An X-ray Powder Diffractogram (XRPD) for Vericiguat Form VT2

An X-ray Powder Diffractogram (XRPD) for Vericiguat Form VT3

An X-ray Powder Diffractogram (XRPD) for Vericiguat Form VT4

An X-ray Powder Diffractogram (XRPD) For Vericiguat Hydrochloride Form VTHCl2

$^{13}C$ Solid State NMR Spectrum of Form VT1 of Vericiguat (At The Range of 0-100 ppm)

$^{13}C$ Solid State NMR Spectrum of Form VT1 of Vericiguat (At The Range of 100-200 ppm)

SOLID STATE FORMS OF VERICIGUAT AND PROCESS FOR PREPARATION THEREOF

CROSS REFERENCE TO RELATED APPLICATIONS

This application is a National Stage of, and claims priority to and the benefit of, International Patent Application No. PCT/US2022/042129, filed Aug. 31, 2022, which, in turn, claims the benefit of and priority to, U.S. Provisional Application No. 63/238,842, filed on Aug. 31, 2021; Indian Provisional Application No. 202211018976, filed on Mar. 30, 2022; Indian Provisional Application No. 202211023924, filed on Apr. 22, 2022; and Indian Provisional Application No. 202211039187, filed on Jul. 7, 2022, the entire disclosures of each of which are incorporated by reference herein.

FIELD OF THE INVENTION

The present disclosure encompasses solid state forms of Vericiguat, in embodiments crystalline polymorphs of Vericiguat, processes for preparation thereof, and pharmaceutical compositions thereof.

BACKGROUND OF THE INVENTION

Vericiguat has the chemical name Methyl {4,6-diamino-2-[5-fluoro-1-(2-fluorobenzyl)-1H-pyrazolo[3,4-b]pyridin-3-yl]pyrimidin-5-yl}carbamate. Vericiguat has the following chemical structure:

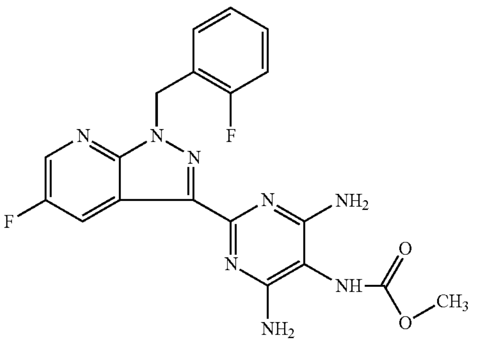 [SMILES: COC(=O)Nc1c(N)nc(-c2nn(Cc3ccccc3F)c3ncc(F)cc23)nc1N]

Vericiguat is a soluble guanylate cyclase (sGC) stimulator and is approved for reducing the risk of cardiovascular death and heart failure (HF) hospitalization following a hospitalization for heart failure or need for outpatient IV diuretics, in adults with symptomatic chronic HF and ejection fraction less than 45%.

Vericiguat is disclosed in WO 2011/147809 (referred to herein as WO '809). WO'809 also discloses hydrochloride, sulphate, phosphate, mesylate, ethane-1,2-disulphonate, maleate and nitrate salts of Vericiguat. WO2013/076168 discloses solid state forms, a di-dimethyl sulphoxide solvate, a dimethylformamide/water solvate, a triacetic acid solvate, a monohydrate and a dihydrate of Vericiguat.

Polymorphism, the occurrence of different crystal forms, is a property of some molecules and molecular complexes. A single compound, like Vericiguat, may give rise to a variety of polymorphs having distinct crystal structures and physical properties like melting point, thermal behaviors (e.g. measured by thermogravimetric analysis—"TGA", or differential scanning calorimetry—"DSC"), X-ray powder diffraction (XRPD) pattern, infrared absorption fingerprint, Raman absorption fingerprint, and solid state (13C-)NMR spectrum. One or more of these techniques may be used to distinguish different polymorphic forms of a compound.

Different solid state forms (including solvated forms) of an active pharmaceutical ingredient may possess different properties. Such variations in the properties of different solid state forms and solvates may provide a basis for improving formulation, for example, by facilitating better processing or handling characteristics, improving the dissolution profile, or improving stability (polymorph as well as chemical stability) and shelf-life. These variations in the properties of different solid state forms may also provide improvements to the final dosage form, for instance, if they serve to improve bioavailability. Different solid state forms and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new solid state forms and solvates of a pharmaceutical product can provide materials having desirable processing properties, such as ease of handling, ease of processing, storage stability, and ease of purification or as desirable intermediate crystal forms that facilitate conversion to other polymorphic forms. New polymorphic forms and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life.

For at least these reasons, there is a need for additional solid state forms (including solvated forms) of Vericiguat.

SUMMARY OF THE INVENTION

The present disclosure provides crystalline polymorphs or salts of Vericiguat, particularly Vericiguat hydrochloride, processes for preparation thereof, and pharmaceutical compositions thereof. These crystalline polymorphs can be used to prepare other solid state forms of Vericiguat, Vericiguat salts, particularly Vericiguat hydrochloride and their solid state forms.

The present disclosure also provides uses of the said solid state forms of Vericiguat and salts thereof, particularly Vericiguat hydrochloride of the present disclosure, in the preparation of other solid state forms of Vericiguat and/or Vericiguat co-crystals and/or salts, particularly Vericiguat hydrochloride thereof, and their solid state forms thereof. In embodiments, the present disclosure provides crystalline forms of Vericiguat designated as Form V1, V2, V3, V4, V5, V6, VT1, VT2, VT3 and/or Form VT4 (defined herein) and crystalline forms of Vericiguat hydrochloride designated as Form VTHCl1 and/or VTHCl2 (defined herein).

The present disclosure relates to solid state forms of Vericiguat or salts of Vericiguat particularly Vericiguat hydrochloride, processes for preparation thereof, and pharmaceutical compositions comprising these solid state forms.

The present disclosure also provides use of the solid state forms of Vericiguat or salts of Vericiguat particularly Vericiguat hydrochloride, for preparing other solid state forms of Vericiguat and/or Vericiguat salts, and their solid state forms thereof.

The present disclosure provides crystalline polymorphs of Vericiguat and salts of Vericiguat, particularly Vericiguat hydrochloride for use in medicine, including for the treatment of chronic heart failure.

The present disclosure also provides solid state forms of Vericiguat or salts of Vericiguat particularly Vericiguat hydrochloride of the present disclosure for use in the preparation of other solid state forms of Vericiguat and/or Vericiguat salts, and their solid state forms thereof.

The present disclosure further provides processes for preparing other solid state forms of Vericiguat and/or salts, and their solid state forms thereof.

In another embodiment, the present disclosure encompasses the described solid state forms of Vericiguat or salts of Vericiguat particularly Vericiguat hydrochloride, in the preparation of pharmaceutical compositions and/or formulations, optionally for the treatment of chronic heart failure.

In another embodiment, the present disclosure encompasses use of the described solid state form of Vericiguat and salts of Vericiguat, particularly Vericiguat hydrochloride of the present disclosure for the preparation of pharmaceutical compositions and/or formulations.

The present disclosure further provides pharmaceutical compositions comprising any one or a combination of the solid state form of Vericiguat and salts of Vericiguat, particularly Vericiguat hydrochloride according to the present disclosure.

In yet another embodiment, the present disclosure encompasses pharmaceutical formulations comprising any one or a combination of the described solid state forms of Vericiguat or salts of Vericiguat particularly Vericiguat hydrochloride, and at least one pharmaceutically acceptable excipient.

The present disclosure includes processes for preparing the above mentioned pharmaceutical compositions. The processes include combining any one or a combination of the crystalline polymorphs of Vericiguat and salts of Vericiguat, particularly Vericiguat hydrochloride with at least one pharmaceutically acceptable excipient.

The present disclosure encompasses processes to prepare said pharmaceutical formulations of Vericiguat comprising combining any one or a combination of the described solid state forms at least one pharmaceutically acceptable excipient.

The solid state forms of Vericiguat and salts of Vericiguat, particularly Vericiguat hydrochloride as defined herein defined herein as well as the pharmaceutical compositions or formulations of the solid state form of Vericiguat particularly Vericiguat hydrochloride can be used as medicaments, particularly for the treatment of for the treatment of chronic heart failure.

The present disclosure also provides methods of treating chronic heart failure, by administering a therapeutically effective amount of any one or a combination of the crystalline polymorphs of Vericiguat and salts of Vericiguat, particularly Vericiguat hydrochloride of the present disclosure, or at least one of the above pharmaceutical compositions, to a subject suffering from chronic heart failure, or otherwise in need of the treatment.

The present disclosure also provides uses of crystalline polymorphs of Vericiguat and salts of Vericiguat, particularly Vericiguat hydrochloride of the present disclosure, or at least one of the above pharmaceutical compositions, for the manufacture of medicaments for treating e.g. chronic heart failure.

DETAILED DESCRIPTION OF THE INVENTION

Figure 1:
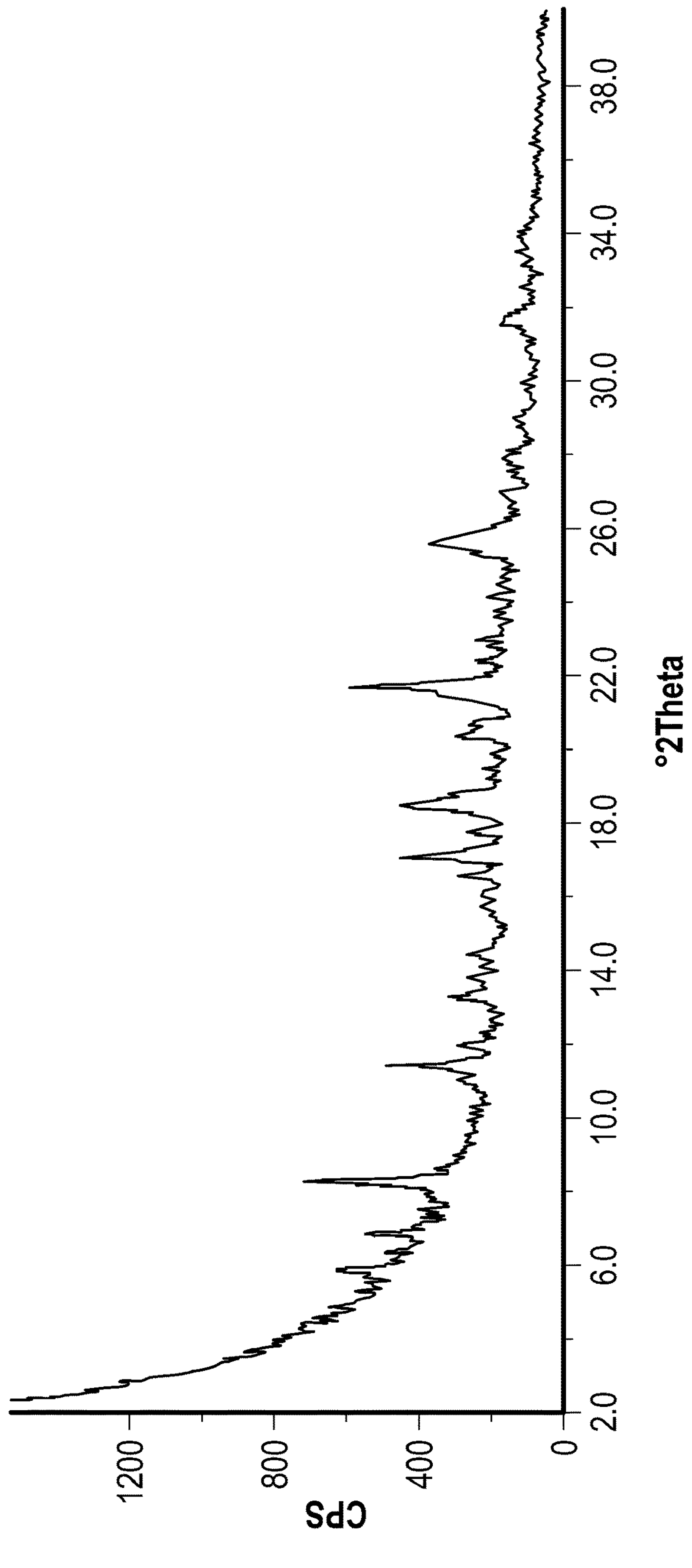
FIG. 1 shows an X-ray powder diffractogram (XRPD) of form V1 of Vericiguat.

The present disclosure relates to solid state forms of Vericiguat, including crystalline polymorphs of Vericiguat and salts of Vericiguat, particularly Vericiguat hydrochloride, processes for preparation thereof, pharmaceutical compositions thereof and pharmaceutical compositions and formulations comprising these solid state forms and/or combinations thereof.

Solid state properties of Vericiguat and salts of Vericiguat, particularly Vericiguat hydrochloride and crystalline polymorphs thereof can be influenced by controlling the conditions under which Vericiguat and crystalline polymorphs thereof are obtained in solid form.

The solid state form of Vericiguat according to the present disclosure may have advantageous properties selected from at least one of: chemical or polymorphic purity, flowability, solubility, wettability, low hygroscopicity, low solvent (e.g. water) content, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, or bulk density.

A crystal form may be referred to herein as being characterized by graphical data "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Vericiguat and salts of Vericiguat, particularly Vericiguat hydrochloride referred to herein as being characterized by graphical data "as depicted in" a Figure will thus be understood to include any crystal forms of the Vericiguat, and salts of Vericiguat, particularly Vericiguat hydrochloride characterized with the graphical data having such small variations, as are well known to the skilled person, in comparison with the Figure.

A solid state form (or polymorph) of Vericiguat as described in any aspect or embodiment of the present disclosure may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, a crystalline polymorph of Vericiguat described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject crystalline polymorph of Vericiguat. In some embodiments of the disclosure, the described crystalline polymorph of Vericiguat may contain from about 1% to about 20% (w/w), from about 5% to about 20% (w/w), or from about 5% to about 10% (w/w) of one or more other crystalline polymorph of the same Vericiguat.

A solid state form (or polymorph) of Vericiguat as described in any aspect or embodiment of the present disclosure may be a purified form. As used herein, the term "purified" refers to a compound that is substantially free of impurities as well as artifacts of the preparative process. Generally a "purified" compound or composition has a purity of at least 95%, 96%, 97%, 98%, 98.5%, 99%, 99.2%, 99.4%, 99.6%, 99.8% or 99.9% relative to other components (impurities).

As used herein, unless stated otherwise, XRPD peaks reported herein are optionally measured using CuK α radiation, λ=1.5418 Å. XRPD peaks reported herein are measured using CuK α radiation, λ=1.5418 Å, typically at a temperature of 25±3° C.

As used herein, unless stated otherwise, 13C NMR reported herein are measured at 125 MHz at a magic angle spinning frequency $\omega_r/2\pi$=11 kHz, preferably at a temperature of at 293 K±3° C.

As used herein, the term "isolated" in reference to solid state forms of Vericiguat and salts of Vericiguat, particularly Vericiguat hydrochloride of the present disclosure corresponds to solid state form of Vericiguat and salts of Vericiguat, particularly Vericiguat hydrochloride that is physically separated from the reaction mixture in which it is formed.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

As used herein, unless indicated otherwise, the term "elevated temperature" refers to any temperature above room temperature, preferably above about 20° C., and more preferably above about 25° C.

A process or step may be referred to herein as being carried out "overnight." This refers to a time interval, e.g., for the process or step, that spans the time during the night, when that process or step may not be actively observed. This time interval is from about 8 to about 20 hours, about 10 to about 18 hours, or about 16 hours.

As used herein, and unless stated otherwise, the term "anhydrous" in relation to crystalline Vericiguat relates to a crystalline Vericiguat and salts of Vericiguat, particularly Vericiguat hydrochloride which does not include any crystalline water (or other solvents) in a defined, stoichiometric amount within the crystal. Moreover, an "anhydrous" form does not contain more than 1% (w/w) of either water or organic solvents as measured for example by TGA. The term "solvate", as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

The amount of solvent employed in a chemical process, e.g., a reaction or crystallization, may be referred to herein as a number of "volumes" or "vol" or "V." For example, a material may be referred to as being suspended in 10 volumes (or 10 vol or 10 V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding methyl tert-butyl ether (MTBE) (1.5 v/v) to a 100 ml reaction mixture would indicate that 150 mL of MTBE was added.

As used herein, the term "reduced pressure" refers to a pressure that is less than atmospheric pressure. For example, reduced pressure is about 10 mbar to about 50 mbar.

As used herein and unless indicated otherwise, the term "ambient conditions" refer to atmospheric pressure and a temperature of 22-24° C.

The present disclosure includes a crystalline form of Vericiguat designated as Form V1. The crystalline Form V1 of Vericiguat can be characterized by data selected from one or more of the following: an XRPD pattern having peaks at 8.3, 11.4, 13.3, 17.2 and 25.7 degrees 2-theta±0.2 degrees 2-theta; an XRPD pattern as depicted in FIG. 1; and combinations of these data.

Crystalline Form V1 of Vericiguat may be further characterized by the XRPD pattern having peaks at 8.3, 11.4, 13.3, 17.2 and 25.7 degrees 2-theta±0.2 degrees 2-theta, and also having one, two, three, four or five additional peaks selected from 5.9, 6.9, 16.6, 17.8 and 18.5 degrees two theta±0.2 degrees two theta. Alternatively, crystalline Form V1 of Vericiguat may be characterized by an XRPD pattern having peaks at 5.9, 6.9, 8.3, 11.4, 13.3, 16.6, 17.2, 17.8, 18.5, and 25.7 degrees 2-theta±0.2 degrees 2-theta, Crystalline Form V1 of Vericiguat may be characterized by each of the above characteristics alone/or by all possible combinations, e.g. by XRPD pattern having peaks at 8.3, 11.4, 13.3, 17.2 and 25.7 degrees 2-theta±0.2 degrees 2-theta and an XRPD pattern as depicted in FIG. 1.

In one embodiment of the present disclosure, Crystalline Form V1 of Vericiguat is isolated.

The step of isolating Crystalline Form V1 of Vericiguat may be performed by lyophilization. Optionally, crystalline Form V1 Vericiguat may be prepared by lyophilization of a solution of Vericiguat in a solvent, preferably dimethyl sulphoxide.

The present disclosure includes a crystalline form of Vericiguat designated as Form V2. The crystalline Form V2 of Vericiguat can be characterized by data selected from one or more of the following: an XRPD pattern having peaks at 4.9, 5.9, 12.9, 14.8 and 20.1 degrees 2-theta±0.2 degrees 2-theta; an XRPD pattern as depicted in FIG. 2; and combinations of these data.

Crystalline Form V2 of Vericiguat may be further characterized by the XRPD pattern having peaks at 4.9, 5.9, 12.9, 14.8 and 20.1 degrees 2-theta±0.2 degrees 2-theta, and also having one, two, three, four or five additional peaks selected from 7.6, 11.7, 15.6, 17.8 and 18.3 degrees two theta±0.2 degrees two theta. Alternatively, crystalline Form V2 of Vericiguat may be characterized by an XRPD pattern having peaks at 4.9, 5.9, 7.6, 11.7, 12.9, 14.8, 15.6, 17.8, 18.3, and 20.1 degrees 2-theta±0.2 degrees 2-theta.

Figure 2:
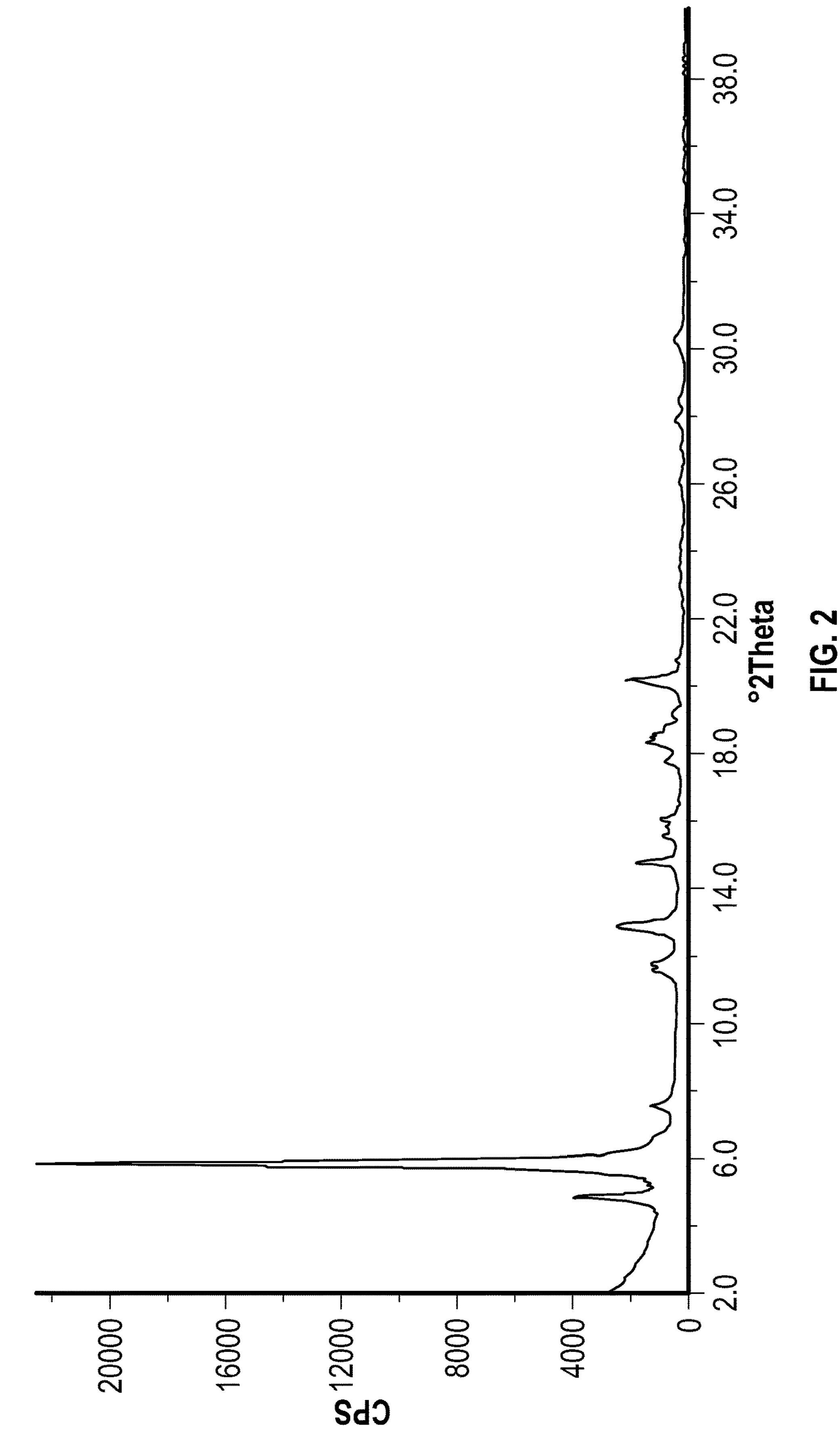
FIG. 2 shows an X-ray powder diffractogram (XRPD) of form V2 of Vericiguat.

Crystalline Form V2 of Vericiguat may be characterized by each of the above characteristics alone/or by all possible combinations, e.g. by XRPD pattern having peaks at 4.9, 5.9, 12.9, 14.8 and 20.1 degrees 2-theta±0.2 degrees 2-theta and an XRPD pattern as depicted in FIG. 2.

In one embodiment of the present disclosure, Crystalline Form V2 of Vericiguat is isolated.

The step of isolating Crystalline Form V2 of Vericiguat may be performed by crystallization. Optionally, crystalline Form V2 may be prepared by crystallisation of Vericiguat from a solvent-antisolvent mixture, particularly 1,2-dioxolane and methyl ethyl ketone or 2-ethoxyethanol and methyl isobutyl ketone. Crystalline Form V2 may alternatively be prepared by crystallisation of Vericiguat from a solution in 2-ethoxyethanol.

The present disclosure includes a crystalline form of Vericiguat designated as Form V3. The crystalline Form V3 of Vericiguat can be characterized by data selected from one or more of the following: an XRPD pattern having peaks at 4.7, 9.7, 11.3, 11.9 and 16.3 degrees 2-theta±0.2 degrees 2-theta; an XRPD pattern as depicted in FIG. 3; and combinations of these data.

Crystalline Form V3 of Vericiguat may be further characterized by the XRPD pattern having peaks at 4.7, 9.7, 11.3, 11.9 and 16.3 degrees 2-theta±0.2 degrees 2-theta, and also having one, two, three, four or five additional peaks selected from 6.3, 15.5, 20.1, 22.7 and 24.4 degrees two theta±0.2 degrees two theta. Alternatively, crystalline Form V3 of Vericiguat may be characterized by an XRPD pattern having peaks at 4.7, 6.3, 9.7, 11.3, 11.9, 15.5, 16.3, 20.1, 22.7 and 24.4 degrees 2-theta±0.2 degrees 2-theta.

Figure 3:
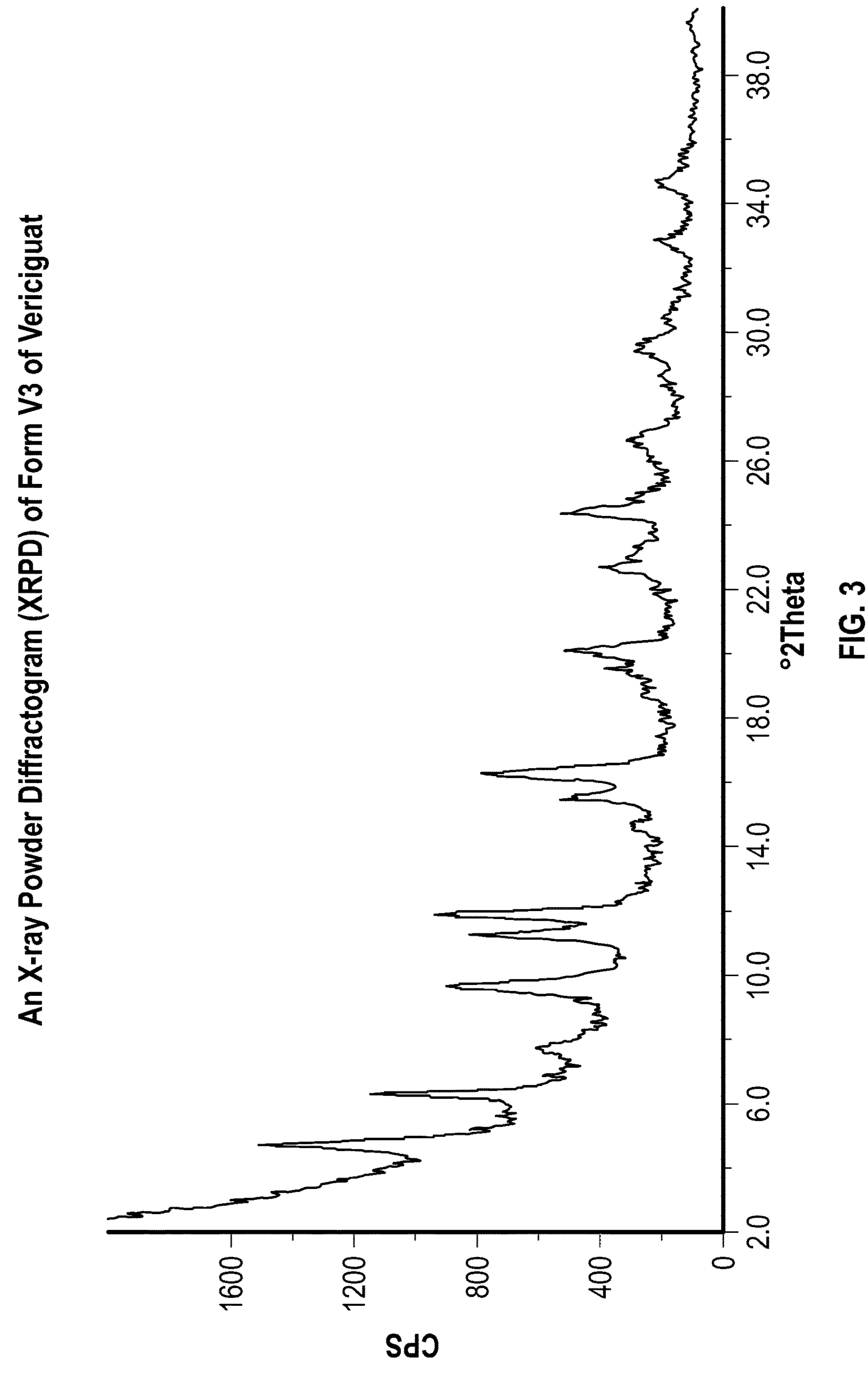
FIG. 3 shows an X-ray powder diffractogram (XRPD) of form V3 of Vericiguat.

Crystalline Form V3 of Vericiguat may be characterized by each of the above characteristics alone/or by all possible combinations, e.g. by XRPD pattern having peaks at 4.7, 9.7, 11.3, 11.9 and 16.3 degrees 2-theta±0.2 degrees 2-theta and an XRPD pattern as depicted in FIG. 3.

In one embodiment of the present disclosure, Crystalline Form V3 of Vericiguat is isolated.

The step of isolating Crystalline Form V3 of Vericiguat may be performed by crystallization. Optionally, crystalline Form V3 may be prepared by crystallisation of Vericiguat from a solution in acetic acid.

The present disclosure includes a crystalline form of Vericiguat designated as Form V4. The crystalline Form V4 of Vericiguat can be characterized by data selected from one or more of the following: an XRPD pattern having peaks at 6.5, 7.3, 8.0, 16.0 and 17.0 degrees 2-theta±0.2 degrees 2-theta; an XRPD pattern as depicted in FIG. 4 and combinations of these data.

Crystalline Form V4 of Vericiguat may be further characterized by the XRPD pattern having peaks at 6.5, 7.3, 8.0, 16.0 and 17.0 degrees 2-theta±0.2 degrees 2-theta, and also having one, two, three, four or five additional peaks selected from 8.4, 17.3, 20.8, 23.1 and 25.5 degrees two theta±0.2 degrees two theta. Alternatively, crystalline Form V4 of Vericiguat may be characterized by an XRPD pattern having peaks at 6.5, 7.3, 8.0, 8.4, 16.0, 17.0, 17.3, 20.8, 23.1, and 25.5 degrees 2-theta±0.2 degrees 2-theta.

Figure 4:
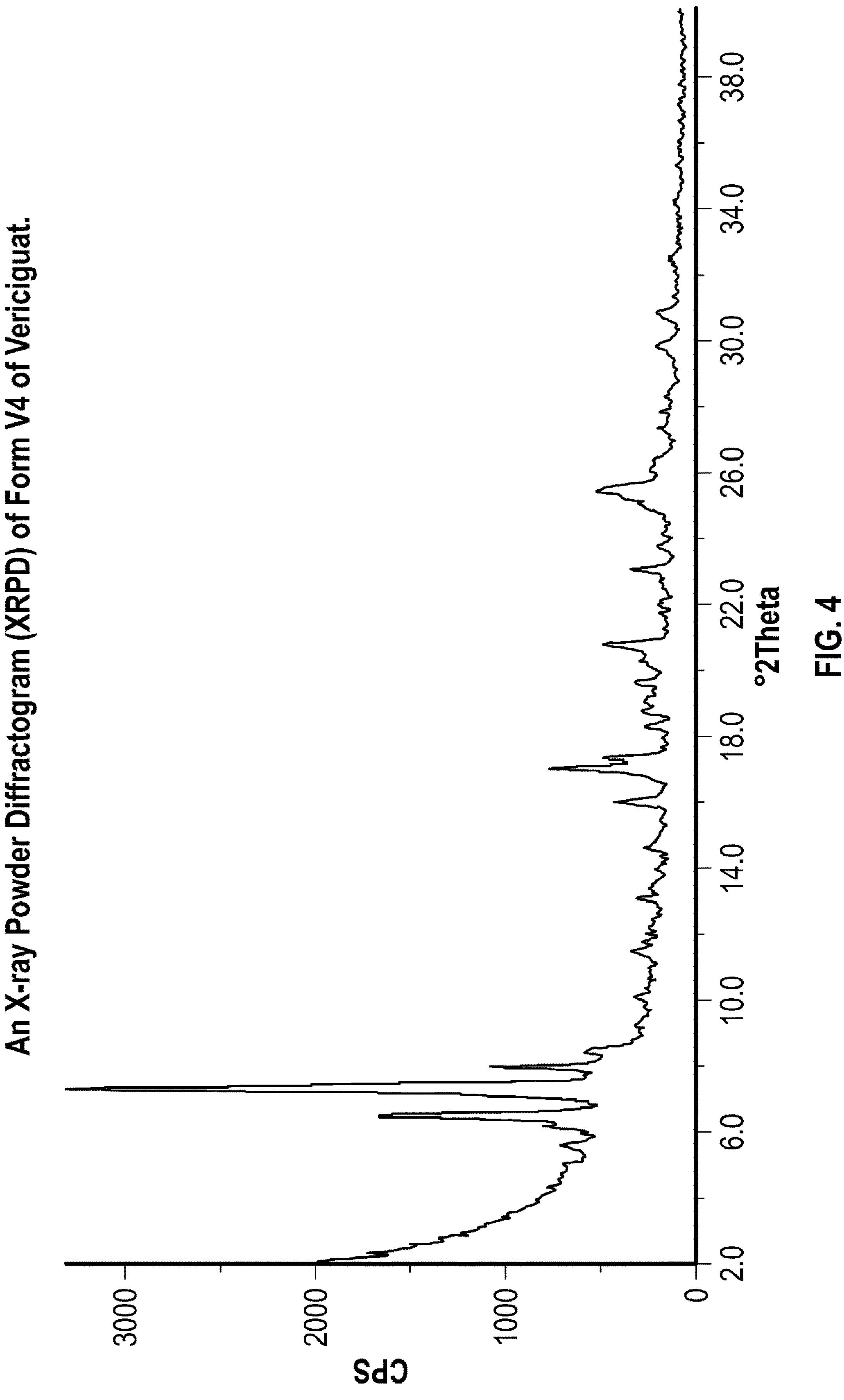
FIG. 4 shows an X-ray powder diffractogram (XRPD) of form V4 of Vericiguat.

Crystalline Form V4 of Vericiguat may be characterized by each of the above characteristics alone/or by all possible combinations, e.g. by XRPD pattern having peaks at 6.5, 7.3, 8.0, 16.0 and 17.0 degrees 2-theta±0.2 degrees 2-theta and an XRPD pattern as depicted in FIG. 4.

In one embodiment of the present disclosure, Crystalline Form V4 of Vericiguat is isolated.

The step of isolating Crystalline Form V4 of Vericiguat may be performed by crystallization. Optionally, crystalline Form V4 may be prepared by crystallisation of Vericiguat, preferably Form V1 in a mixture with propionic acid.

The present disclosure includes a crystalline form of Vericiguat designated as Form V5. The crystalline Form V5 of Vericiguat can be characterized by data selected from one or more of the following: an XRPD pattern having peaks at 5.3, 10.9, 14.1, 17.7 and 19.3 degrees 2-theta±0.2 degrees 2-theta; an XRPD pattern as depicted in FIG. 5; and combinations of these data.

Crystalline Form V5 of Vericiguat may be further characterized by the XRPD pattern having peaks at 5.3, 10.9, 14.1, 17.7 and 19.3 degrees 2-theta±0.2 degrees 2-theta, and also having one, two, three, four or five additional peaks selected from 6.7, 8.8, 10.6, 12.7 and 16.4 degrees two theta±0.2 degrees two theta. Alternatively, crystalline Form V5 of Vericiguat may be characterized by an XRPD pattern having peaks at 5.3, 6.7, 8.8, 10.6, 10.9, 12.7, 14.1, 16.4, 17.7 and 19.3 degrees 2-theta±0.2 degrees 2-theta.

Figure 5:
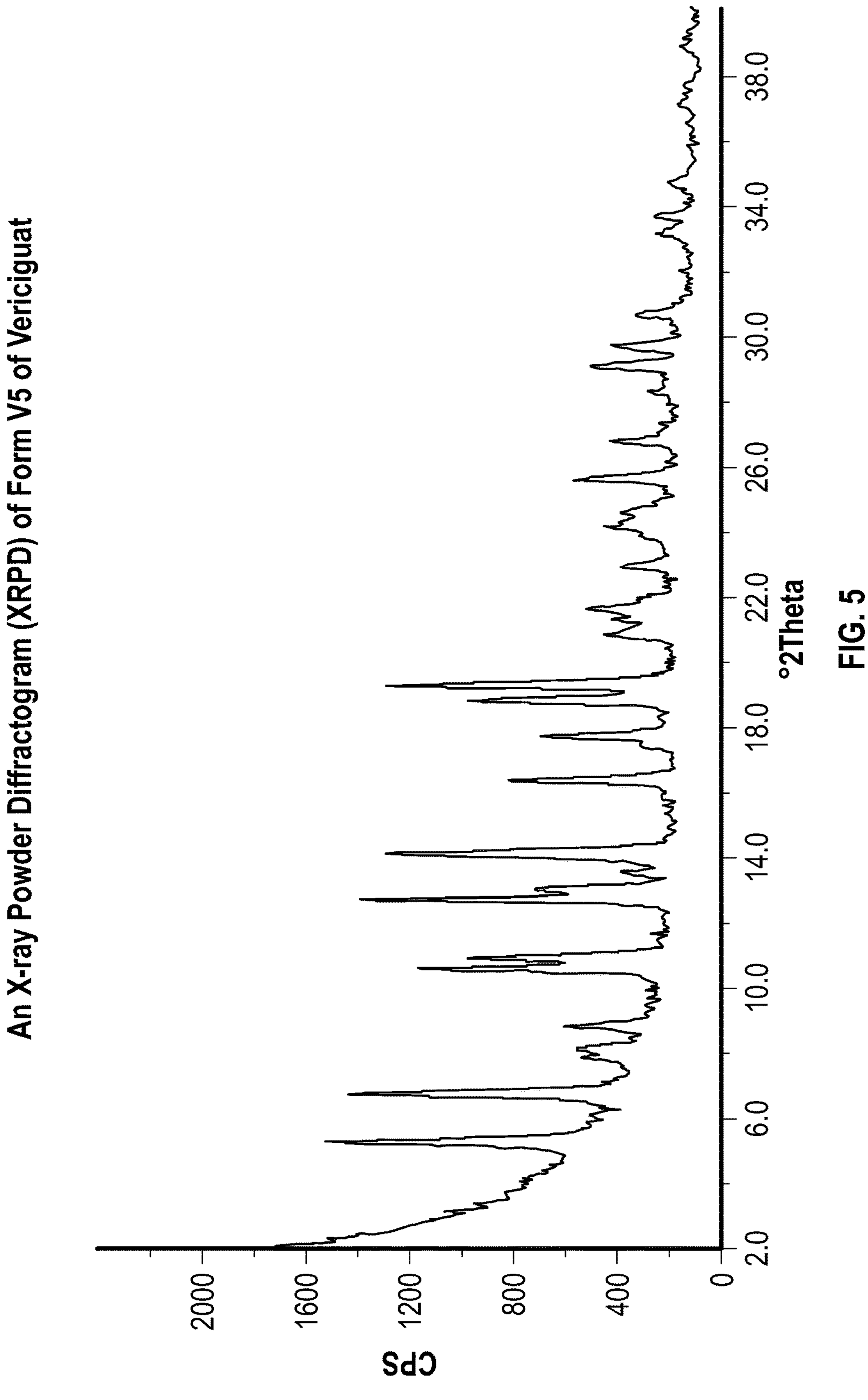
FIG. 5 shows an X-ray powder diffractogram (XRPD) of form V5 of Vericiguat.

Crystalline Form V5 of Vericiguat may be characterized by each of the above characteristics alone/or by all possible combinations, e.g. by XRPD pattern having peaks at 5.3, 10.9, 14.1, 17.7 and 19.3 degrees 2-theta±0.2 degrees 2-theta and an XRPD pattern as depicted in FIG. 5.

In one embodiment of the present disclosure, Crystalline Form V5 of Vericiguat is isolated.

The step of isolating Crystalline Form V5 of Vericiguat may be performed by precipitation. Optionally, crystalline Form V4 may be prepared by crystallisation of Vericiguat from a solution in formic acid.

The present disclosure includes a crystalline form of Vericiguat designated as Form V6. The crystalline Form V6 of Vericiguat can be characterized by data selected from one or more of the following: an XRPD pattern having peaks at 5.7, 7.3, 8.5, 17.1, and 25.4 degrees 2-theta±0.2 degrees 2-theta; an XRPD pattern as depicted in FIG. 6; and combinations of these data.

Crystalline Form V6 of Vericiguat may be further characterized by the XRPD pattern having peaks at 5.7, 7.3, 8.5, 17.1, and 25.4 degrees 2-theta±0.2 degrees 2-theta, and also having one, two, three, four or five additional peaks selected from 11.8, 14.7, 19.2, 19.7, and 26.1 degrees two theta±0.2 degrees two theta. Alternatively, crystalline Form V6 of Vericiguat may be characterized by an XRPD pattern having peaks at 5.7, 7.3, 8.5, 11.8, 14.7, 17.1, 19.2, 19.7, 25.4, and 26.1 degrees 2-theta±0.2 degrees 2-theta.

Figure 6:
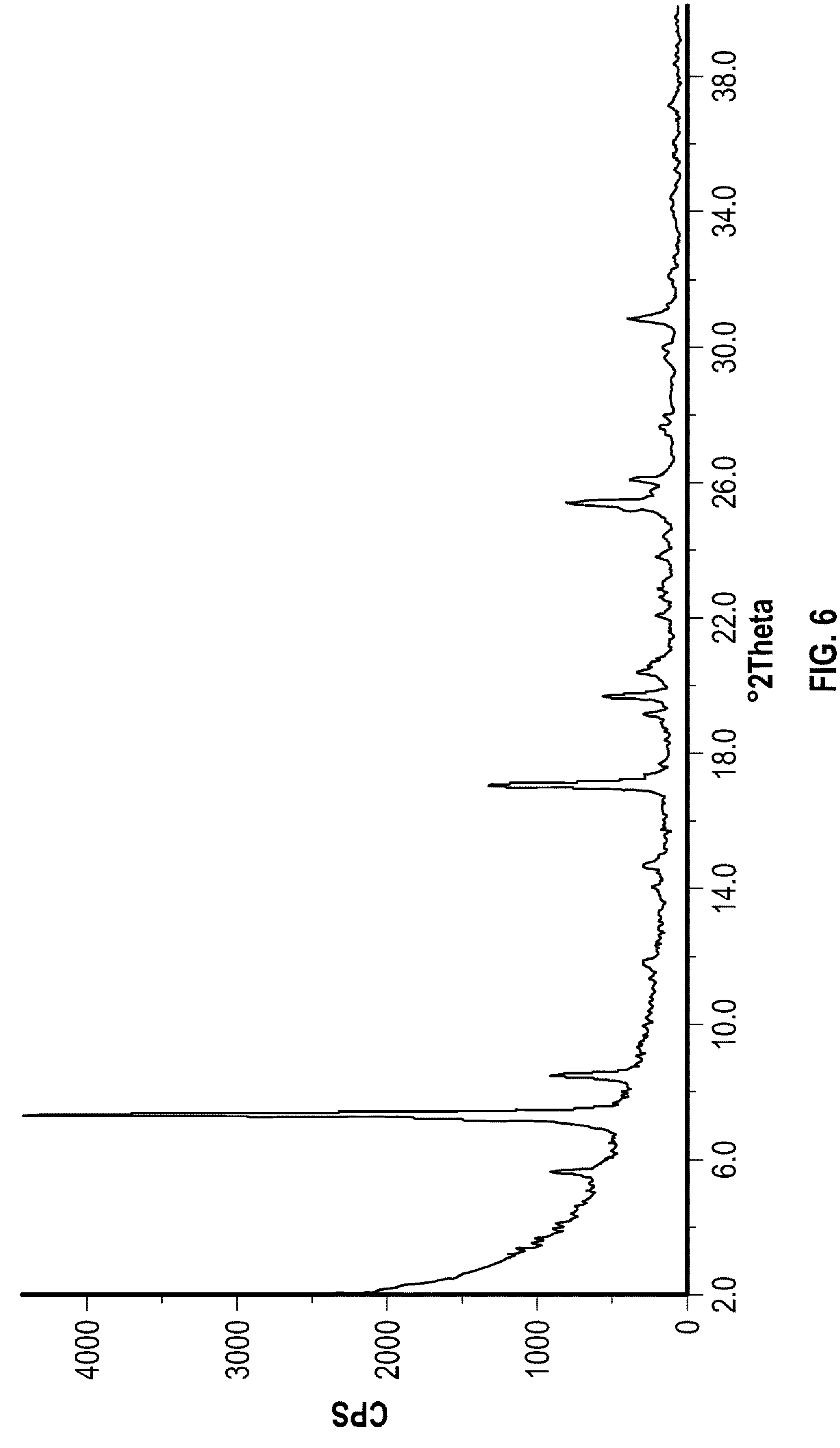
FIG. 6 shows an X-ray powder diffractogram (XRPD) of form V6 of Vericiguat.

Crystalline Form V6 of Vericiguat may be characterized by each of the above characteristics alone/or by all possible combinations, e.g. by XRPD pattern having peaks at 5.7, 7.3, 8.5, 17.1, and 25.4 degrees 2-theta±0.2 degrees 2-theta and an XRPD pattern as depicted in FIG. 6.

In one embodiment of the present disclosure, Crystalline Form V6 of Vericiguat is isolated. Crystalline Form V6 may be isolated by crystallization. Optionally, Form V6 may be prepared by crystallisation of Vericiguat having an XRPD according to FIG. 7 (preferably wherein the Vericiguat is prepared according to example 1, step 1), in a mixture with propionic acid.

Figure 8:
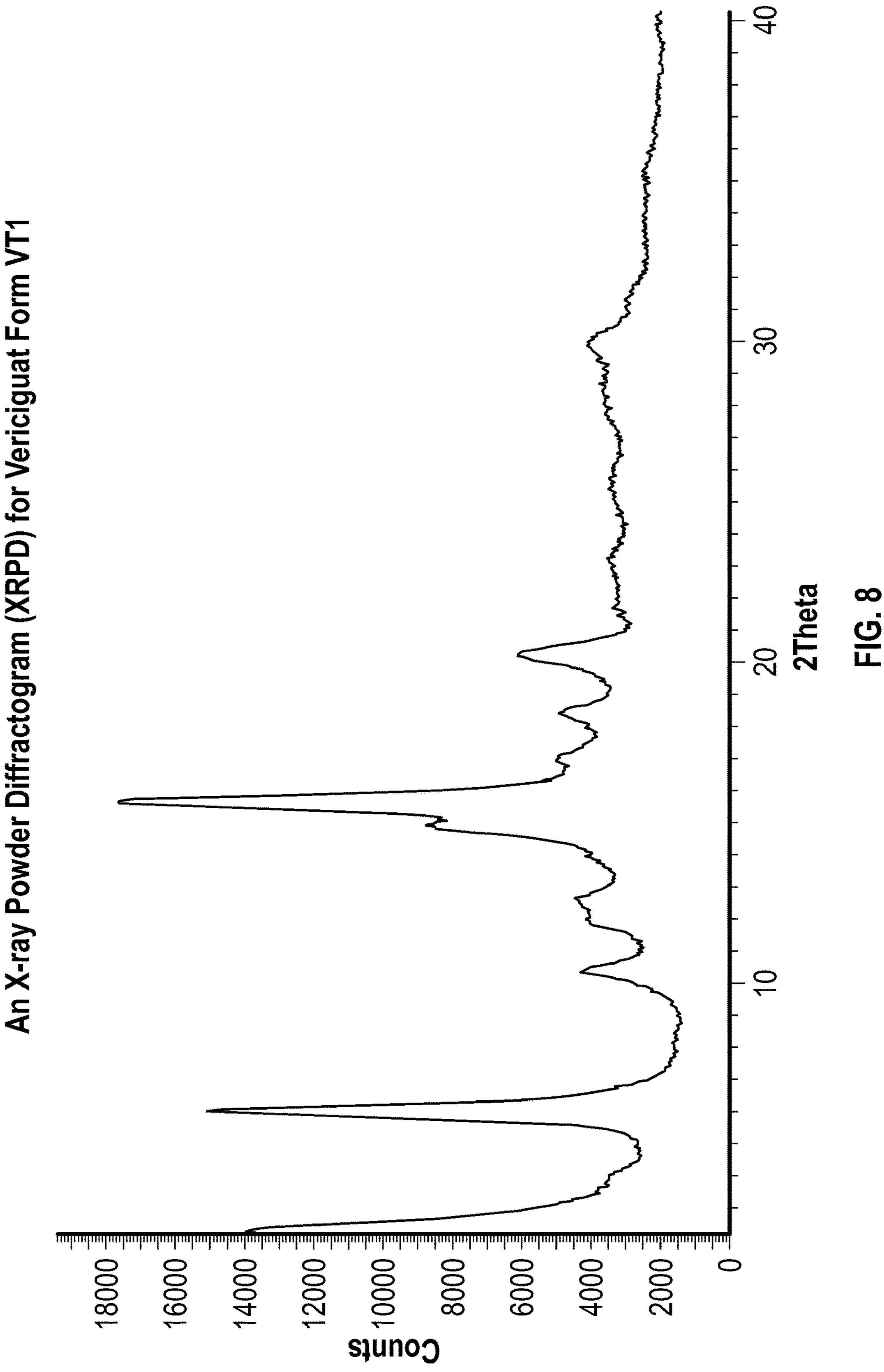
FIG. 8 shows a characteristic X-ray powder diffraction pattern (XRPD) of Vericiguat Form VT1.
Figure 9:
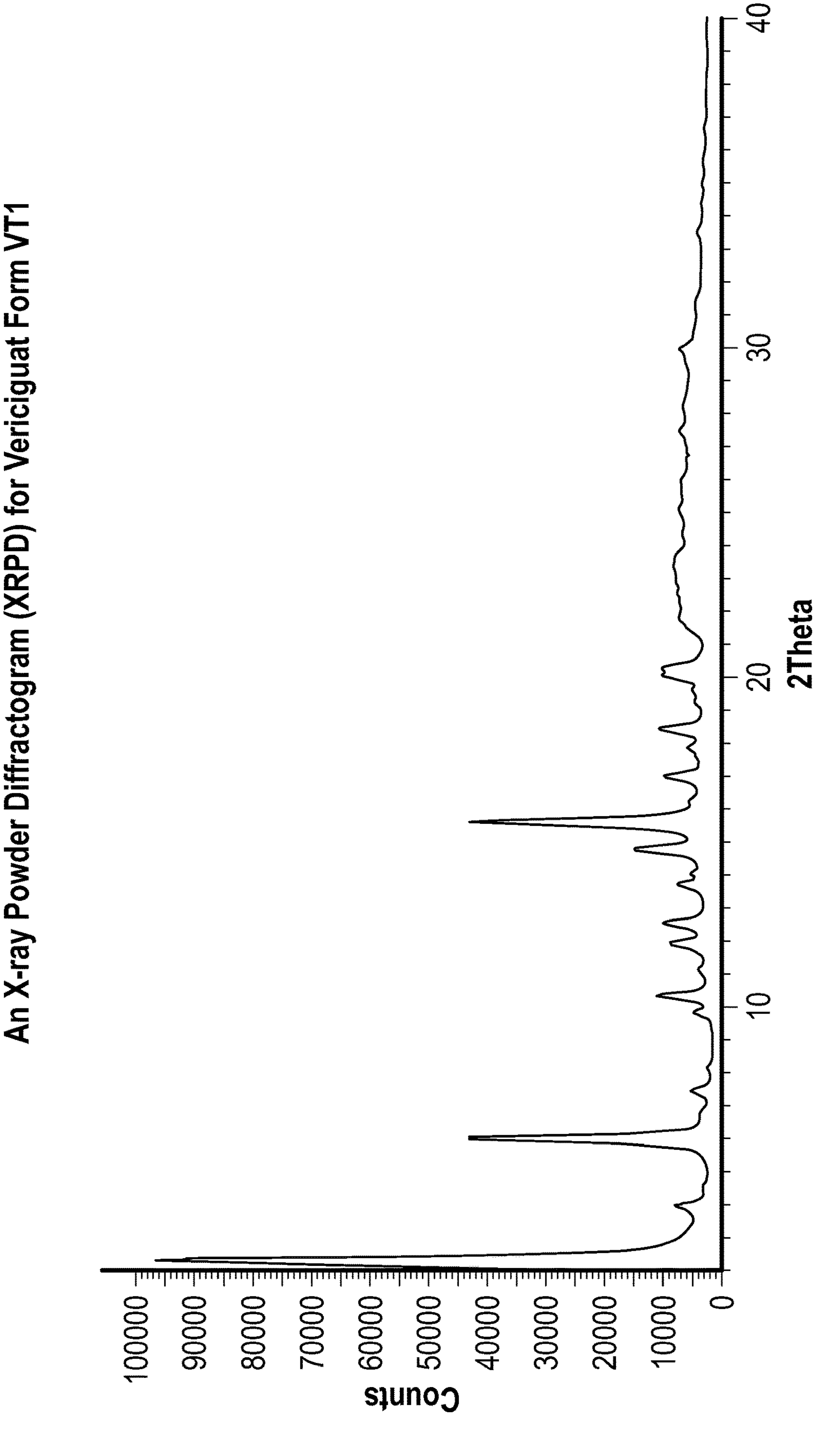
FIG. 9 shows a characteristic X-ray powder diffraction pattern (XRPD) of Form VT1.
Figure 15A:
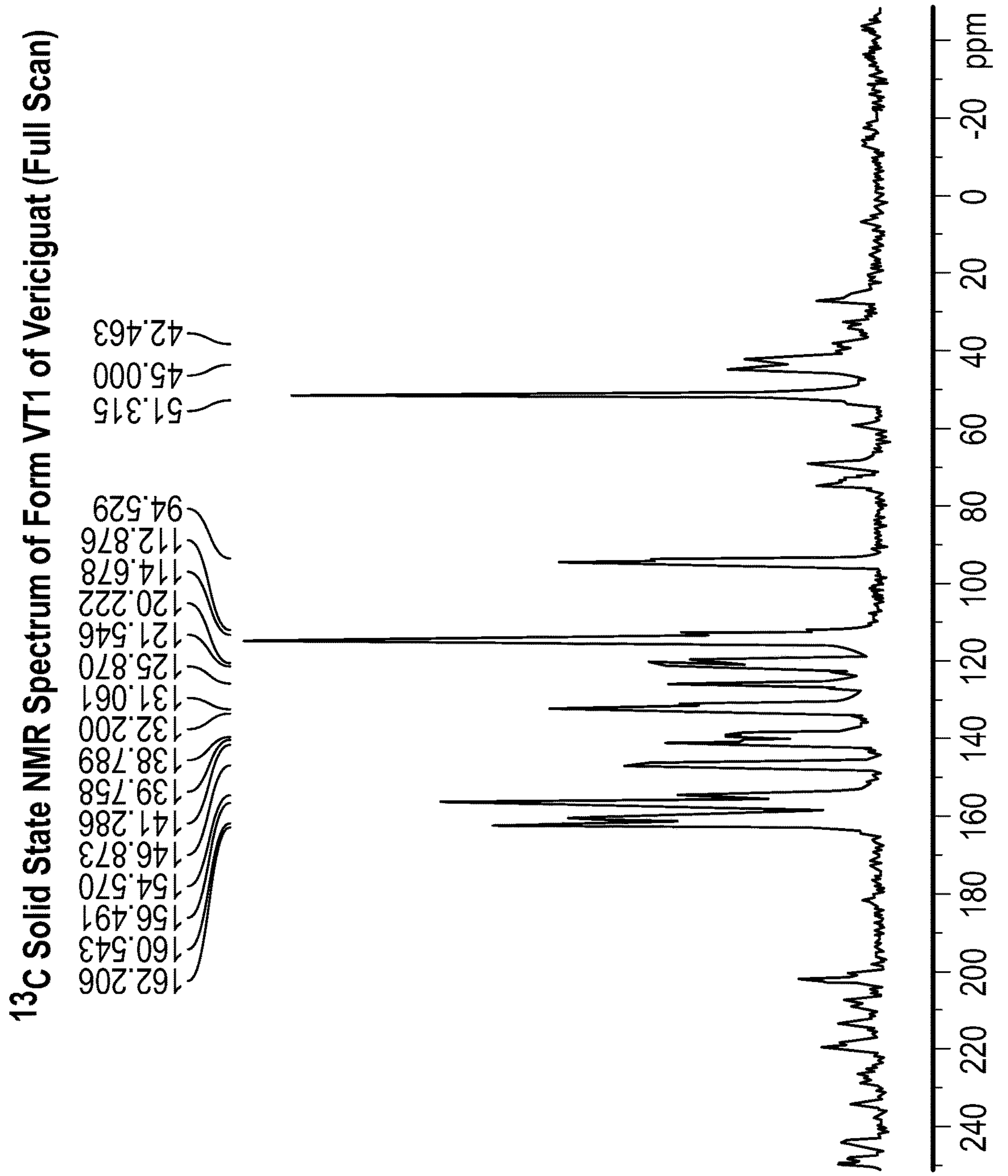
FIG. 15*a* shows $^{13}C$ solid state NMR spectrum of Form VT1 of Vericiguat (full scan).
Figure 15B:
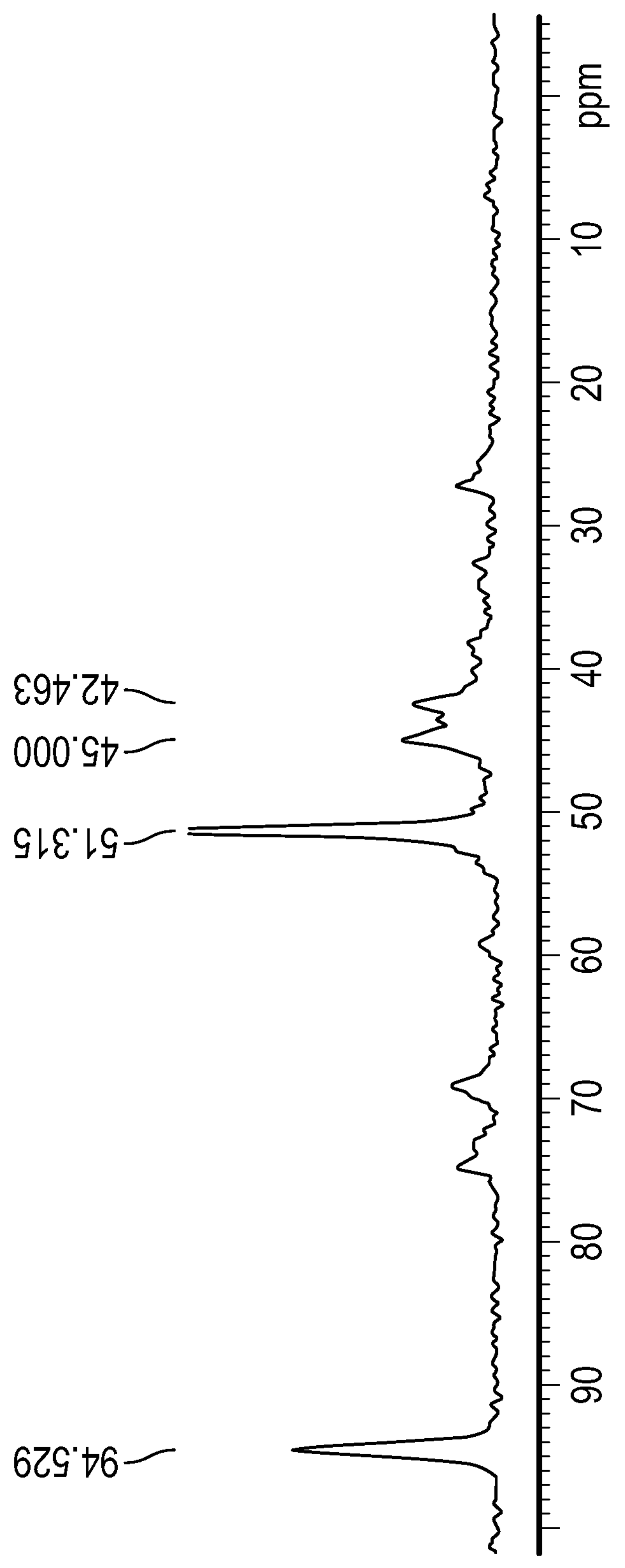
FIG. 15*b* shows $^{13}C$ solid state NMR spectrum of Form VT1 of Vericiguat (at the range of 0-100 ppm).
Figure 15C:
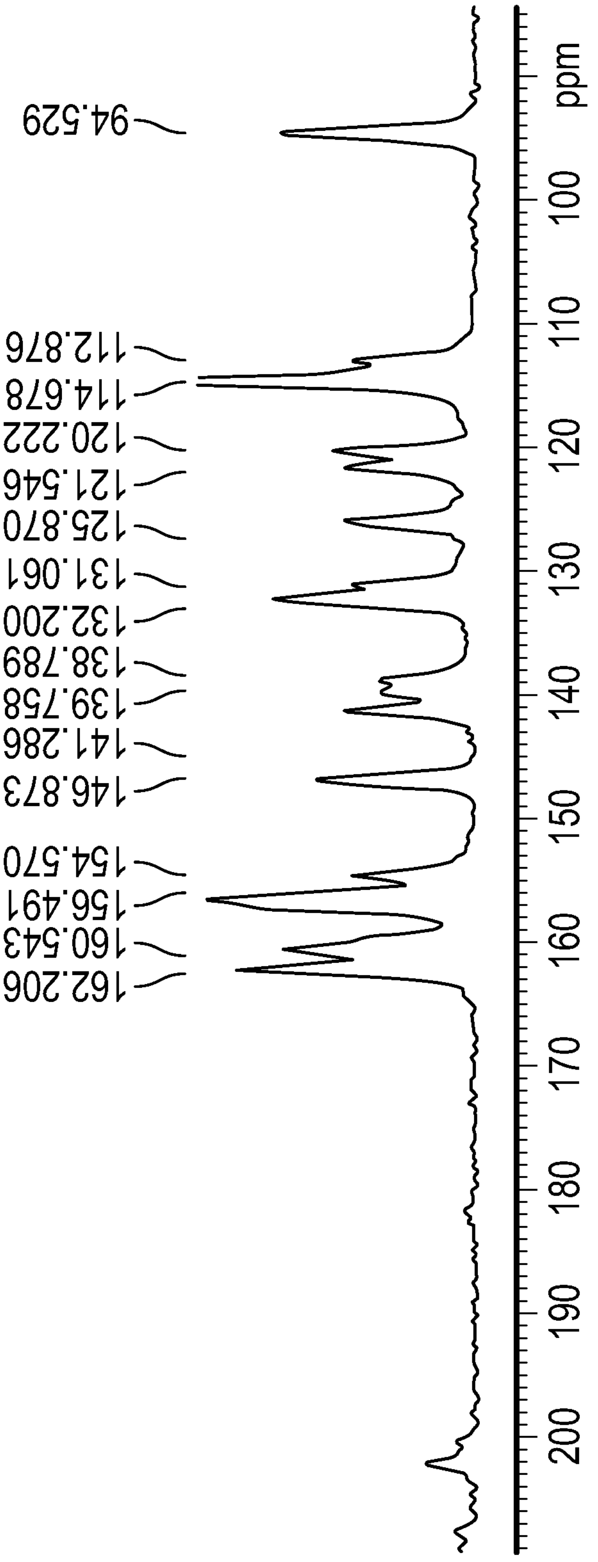
FIG. 15*c* shows $^{13}C$ solid state NMR spectrum of Form VT1 of Vericiguat (at the range of 100-200 ppm).

The present disclosure includes a crystalline polymorph of Vericiguat, designated VT1. The crystalline Form VT1 of Vericiguat may be characterized by data selected from one or more of the following: an X-ray powder diffraction pattern substantially as depicted in FIG. 8 or FIG. 9; an X-ray powder diffraction pattern having peaks at 6.0, 10.3, 15.6, 18.4 and 20.1 degrees 2-theta±0.2 degrees 2-theta; a solid state $^{13}C$ NMR spectrum having peaks at 45.0, 51.3, 114.7, 120.2, 125.9, 139.8 and 160.5 ppm±0.2 ppm; a solid state $^{13}C$ NMR spectrum having the following chemical shift absolute differences from a reference peak at 146.9 ppm±2 ppm of 101.9, 95.6, 32.2, 26.7, 21.0, 7.1 and 13.7 ppm±0.1 ppm; a solid state $^{13}C$ NMR spectrum substantially as depicted in FIG. 15*a*, 15*b* or 15*c*; and combinations of these data.

Crystalline Form VT1 of Vericiguat may be further characterized by an X-ray powder diffraction pattern having peaks at 6.0, 10.3, 15.6, 18.4 and 20.1 degrees 2-theta±0.2 degrees 2-theta, and also having any one, two, or three additional peaks selected from 12.4, 17.0 and 31.1 degrees 2-theta±0.2 degrees 2-theta.

Crystalline Form VT1 of Vericiguat may be alternatively characterized by an X-ray powder diffraction pattern having peaks at 6.0, 10.3, 12.4, 15.6, 17.0, 18.4, 20.1 and 31.1 degrees 2-theta±0.2 degrees 2-theta.

Crystalline Form VT1 of Vericiguat as described according to any aspect or embodiment of the disclosure may be further characterized by an XRPD pattern having an additional peak at 2.3±0.2 degrees 2-theta.

Crystalline Form VT1 of Vericiguat as described according to any aspect or embodiment of the disclosure may be further characterized by an XRPD pattern having an absence of any one, two, three, four or five peaks at: 3.2±0.2 degrees 2-theta, 5.1±0.2 degrees 2-theta, 5.4±0.2 degrees 2-theta, 6.4±0.2 degrees 2-theta, or 6.6±0.2 degrees 2-theta. Alternatively, crystalline Form VT1 as described according to any aspect or embodiment of the disclosure may be characterized by an XRPD pattern having an absence of a peak at 3.2±0.2 degrees 2-theta, or an absence of a peak at 5.1±0.2 degrees 2-theta, or an absence of a peak at 5.4±0.2 degrees 2-theta, or an absence of a peak at 6.4±0.2 degrees 2-theta, or an absence of a peak at 6.6±0.2 degrees 2-theta. Optionally, crystalline Form VT1 as described according to any aspect or embodiment of the disclosure may be characterized by an XRPD pattern having an absence of peaks at: 3.2, 5.1, 5.4, 6.4 and 6.6±0.2 degrees 2-theta.

In one embodiment of the present disclosure, crystalline Form VT1 of Vericiguat is isolated.

Crystalline Form VT1 of Vericiguat may be anhydrous form.

Crystalline Form VT1 of Vericiguat may be characterized by each of the above characteristics alone/or by all possible combinations, e.g., an XRPD pattern having peaks at 6.0, 10.3, 15.6, 18.4 and 20.1 degrees 2-theta±0.2 degrees 2-theta; an XRPD pattern as depicted in FIG. 8 or FIG. 9, and combinations thereof.

The present disclosure further comprises a process for preparation of Form VT1 of Vericiguat. The process comprises crystallizing Vericiguat from a solvent mixture comprising 1,4-dioxane and an ester antisolvent, preferably wherein the ester antisolvent is a $C_4$-$C_8$ ester, more preferably a $C_4$-$C_6$ ester, and particularly wherein the ester antisolvent is selected from isopropyl acetate or n-butyl acetate. In an embodiment, the process may comprise combining a solution of Vericiguat in 1,4-dioxane with the ester antisolvent, optionally cooling the mixture, optionally isolating the Vericiguat Form VT1 and optionally drying. According to any aspect or embodiment, the process for preparing Form VT1 of Vericiguat may comprise:

(a) providing a solution of Vericiguat in 1,4-dioxane;
(b) combining the solution with an ester antisolvent;
(c) optionally maintaining the mixture for suitable period of time;
(d) optionally isolating Form VT1 of Vericiguat; and
(e) optionally drying the Form VT1 of Vericiguat.

In any embodiment of this process, the solution in step (a) may be prepared by dissolving Vericiguat in 1,4-dioxane. The 1,4-dioxane may be at an elevated temperature, preferably at a temperature of: about 35° C. to about 130° C., about 50° C. to about 130° C., about 80° C. to about 120° C., about 90° C. to about 110° C., or about 100° C. According to any aspect or embodiment of the process, the ester antisolvent may be at a temperature of about −10° C. to about 25° C., about −10° C. to about 15° C., about −10° C. to about 15° C., about −5° C. to about 5° C., about −2° C. to about 2° C., or about 0° C. Preferably, the ester antisolvent is cooled to a below ambient temperature, more preferably: about −5° C. to about 10° C., about −5° C. to about 5° C., about −2° C. to about 2° C., or about 0° C. According to any aspect or embodiment of the process, the 1,4-dioxane may be used in an amount of about 20 ml to about 80 ml, about 30 ml to about 70 ml, about 40 ml to about 60 ml, about 45 ml to about 55 ml, or about 50 ml, per gram of Vericiguat. According to any aspect or embodiment of the process, the ester antisolvent is preferably a $C_4$-$C_8$ ester, more preferably a $C_4$-$C_6$ ester, and particularly an ester selected from isopropyl acetate or n-butyl acetate. According to any aspect or embodiment of the process, the ester is preferably used in an amount of about 40 ml to about 300 ml, about 60 ml to about 250 ml, about 80 ml to about 220 ml, about 100 ml to about 200 ml, about 120 ml to about 180 ml, about 130 ml to about 170 ml, about 140 ml to about 160 ml, or about 150 ml, per gram of Vericiguat. According to any aspect or embodiment of the process, the ratio (vol:vol) of 1,4-dioxane to ester is: about 2:1 to about 1:8, about 1:1 to about 1:6, about 1:2 to about 1:5, about 1:2 to about 1:4, about 1.25 to about 1.35, or about 1:3. Step (b) may comprise adding the ester to the solution of Vericiguat in 1,4-dioxane or adding the solution of Vericiguat in 1,4-dioxane to the ester. Preferably step (b) comprises adding the solution of Vericiguat in 1,4-dioxane which is at an elevated temperature, to the cooled ester. The process may further comprise maintaining the mixture for a suitable period of time according to step (c). The mixture is preferably maintained under cooling, preferably at a temperature of about −10° C. to about 25° C., about −10° C. to about 15° C., about −5° C. to about 10° C., about −5° C. to about 5° C., about −2° C. to about 2° C., or about 0° C. The mixture may be stirred, and maintained for a period of about 0.5 hours to about 6 hours, about 1 hour to about 4 hours, or about 2 hours. The Vericiguat Form VT1 may be isolated, preferably by any suitable process, such as decantation, filtration or by centrifuge, preferably by filtration. The filtering may be carried out at a temperature of about −5° C. to about 5° C., about 3° C. to about −1° C., or about 0° C.

In any embodiment of this process, the crystalline Form VT1 of Vericiguat may be dried. The crystalline Form VT1 of Vericiguat may be dried, typically at a temperature of about 20° C. to about 60° C., about 25° C. to about 55° C., about 25° C. The drying may be carried out for any suitable time to remove the solvent, typically about 1 to about 5 hours, about 1.5 hours to about 4 hours, or about 2 hours to about 3 hours, or about 30 minutes. The crystalline Form VT1 of Vericiguat may be dried under vacuum, typically at a temperature of about 40° C. to about 80° C., about 50° C. to about 70° C., about 60° C. The drying may be carried out for any suitable time to remove the solvent, typically about 1 to about 5 hours, about 1.5 hours to about 4 hours, or about 2 hours. After isolating, the Form VT1 of Vericiguat may be dried. The drying may be conducted at reduced pressure or under vacuum. The drying may be conducted at any suitable temperature, particularly at: about 30° C. to about 100° C., about 40° C. to about 80° C., about 50° C. to about 70° C., about 55° C. to about 65° C., or about 60° C. The drying may be conducted for a suitable period of time to remove the solvents, preferably for: about 0.5 hours to about 6 hours, about 1 hour to about 5 hours, about 1.5 to about 4 hours, or about 2 hours. In any aspect or embodiment of this process as described herein, the process may comprise:

(a) dissolving Vericiguat in 1,4-dioxane to form a solution;
(b) adding the solution to a cooled ester antisolvent;
(c) cooling;
(d) filtering; and
(e) optionally drying;

wherein the ester antisolvent, and steps (a), (b), (c), (d) and (e) are as described according to any embodiment described above. Preferably, the process may comprise:

(a) dissolving Vericiguat in 1,4-dioxane in an amount of about 40 ml to about 60 ml, at a temperature of about 80° C. to about 120° C., to form a solution;
(b) adding the solution to isopropyl acetate or n-butyl acetate ester, wherein the ester has been cooled to −10° C. to about 15° C.;
(c) cooling the mixture to −10° C. to about 15° C.;
(d) filtering; and
(e) optionally drying.

The present disclosure further comprises an alternative process for the preparation of Form VT1 of Vericiguat. The process comprises crystallisation of Vericiguat from a solution in tetrahydrofuran (THF). Preferably, the process comprises:

(a) concentrating a solution of Vericiguat in THF;
(b) optionally isolating the Vericiguat Form VT1; and
(c) optionally drying.

In any embodiment of this process, the solution in step (a) may be prepared by dissolving Vericiguat in THF. The THF may be at an elevated temperature, preferably at a temperature of: about 35° C. to about 66° C., about 40° C. to about 65° C., about 50° C. to about 65° C., about 55° C. to about 62° C., or about 60° C. The THF is preferably used in an amount of about 100 ml to about 800 ml, about 200 ml to about 750 ml, about 300 ml to about 700 ml, about 450 ml to about 600 ml, about 480 ml to about 550 ml, or about 500 ml, per gram of Vericiguat. Step (a) may comprise distillation of THF from the solution, preferably under reduced pressure. The distillation may be conducted at a temperature of: about 35° C. to about 66° C., about 40° C. to about 65° C., about 50° C. to about 65° C., about 55° C. to about 62° C., or about 60° C. The concentrating may comprise distilling the THF either partially or, preferably substantially to dryness, to form a solid. Preferably the concentrating is carried out to remove substantially all of the THF. After cooling, the Vericiguat Form VT1 may be isolated. Optionally, step (b) comprises isolating the Vericiguat Form VT1 by cooling and washing with an antisolvent. Preferably the cooling is to a temperature of: about 10° C. to about 30° C., about 15° C. to about 28° C., or about 20° C. to about 25° C. Preferably, according to any embodiment of this process, the antisolvent in step (b) may be a $C_4$ to $C_8$ ether, a $C_4$ to $C_5$ ether, a $C_4$ to $C_5$ ether, and preferably methyl tert-butyl ether. The antisolvent may be used in an amount of: about 30 ml to about 140 ml, about 50 ml to about 130 ml, about 70 ml to about 120 ml, about 90 ml to about 110 ml, or about 100 ml, per gram of Vericiguat. After washing, the Vericiguat Form VT1 may be collected by filtration. The filtration is preferably conducted at a temperature of: about 10° C. to about 30° C., about 15° C. to about 28° C., or about 20° C. to about 25° C. After isolating, the Form VT1 of Vericiguat may be dried. The drying may be conducted at reduced pressure or under vacuum. The drying may be conducted at any suitable temperature, particularly at: about 30° C. to about 100° C., about 40° C. to about 80° C., about 50° C. to about 70° C., about 55° C. to about 65° C., or about 60° C. The drying may be conducted for a suitable period of time to remove the solvents, preferably for: about 0.5 hours to about 6 hours, about 1 hour to about 5 hours, about 1.5 to about 4 hours, or about 2 hours. In any embodiment of this process, Vericiguat Form VT1 may be prepared by a process comprising:

(a) distillation of the THF from a solution of Vericiguat in THF to form a solid;
(b) isolating Vericiguat Form VT1 by cooling, washing and filtering; and
(c) optionally drying.

The solution of Vericiguat in THF may be prepared by dissolving Vericiguat in THF, preferably at elevated temperature, particularly at a temperature of about 40° C. to about 80° C., or about 50° C. to about 70° C., or about 60° C. The THF may be removed by distilling the solution, preferably at a temperature of about 55° C. to about 70° C., or about 60° C., preferably wherein the distilling is conducted under reduced pressure. The distillation may be conducted for a sufficient time to remove most of the solvent, and optionally to form a solid. Particularly, the distillation may be carried out over a period of about 5 minutes to about 1 hour, about 10 minutes to about 30 minutes, or about 15 minutes. The THF may be used in an amount of about 200 ml to about 700 ml, about 300 ml to about 600 ml, or about 500 ml, per gram of Vericiguat. The cooling in step (b) may be to a temperature of about 20° C.

to about 25° C. In any embodiment of the process, the washing step (b) may be carried out using methyl tert-butyl ether. The methyl tert-butyl ether may be used in an amount of about 50 ml to about 150 ml, about 80 ml to about 120 ml, or about 100 ml, per gram of Vericiguat. The filtering in step (b) may be conducted at a temperature of about 5° C. to about 40° C., about 15° C. to about 30° C., or about 20° C. to about 25° C.

The present disclosure provides a further alternative process for the preparation of Form VT1 of Vericiguat. The process comprises crystallising Vericiguat from a solvent mixture comprising dimethyl acetamide (DMAc) and isopropyl acetate (IPAc). In an embodiment, the process may comprise combining a solution of Vericiguat in DMAc, with IPAc, optionally cooling the mixture, optionally isolating the Vericiguat Form VT1 and optionally drying. According to any aspect or embodiment of this process, Form VT1 of Vericiguat may be prepared by a process comprising:

(a) providing a solution of Vericiguat in dimethyl acetamide;
(b) combining the solution with isopropyl acetate;
(c) optionally maintaining the mixture for suitable period of time;
(d) optionally isolating Form VT1 of Vericiguat; and
(e) optionally drying the Form VT1 of Vericiguat.

In any embodiment of this process, the solution in step (a) may be prepared by combining Vericiguat and DMAc, and optionally heating the mixture to form a solution. The mixture may be heated to a temperature of: about 35° C. to about 100° C., about 40° C. to about 90° C., about 45° C. to about 80° C., about 50° C. to about 75° C., or about 50° C. to about 60° C. According to any aspect or embodiment of the process, the DMAc may be used in an amount of about 2 ml to about 20 ml, about 4 ml to about 15 ml, about 6 ml to about 12 ml, about 7 ml to about 10 ml, or about 9 ml, per gram of Vericiguat. According to any aspect or embodiment of the process, the IPAc in step (b) is preferably used in an amount of about 10 ml to about 80 ml, about 15 ml to about 70 ml, about 20 ml to about 60 ml, about 30 ml to about 50 ml, about 35 ml to about 45 ml, or about 40 ml, per gram of Vericiguat. According to any aspect or embodiment of the process, the ratio (vol:vol) of DMAc to IPAc is: about 2:1 to about 1:8, about 1:1 to about 1:7, about 1:2 to about 1:6, about 1:3 to about 1:5.5, about 1.35 to about 1.5, or about 1:4. Step (b) may comprise adding the IPAc to the solution of Vericiguat in DMAc or adding the solution of Vericiguat in DMAc to the IPAc. Preferably step (b) comprises adding the solution of Vericiguat in DMAc to the IPAc. Preferably, the addition is dropwise. The addition may preferably be conducted over a period of about 5 minutes to about 120 minutes, about 10 minutes to about 60 minutes, or about 15 minutes to about 30 minutes. The IPAc may be at ambient temperature, preferably at a temperature of about 20° C. to about 35° C., about 23° C. to about 30° C., or about 25° C. to about 27° C. The process may further comprise maintaining the mixture for a suitable period of time according to step (c). The mixture is preferably maintained at a temperature of about 20° C. to about 35° C., about 23° C. to about 30° C., or about 25° C. to about 27° C. The mixture may be stirred, and maintained for a period of: about 0.5 hours to about 4 hours, about 0.6 hours to about 2 hours, or about 0.8 hours to about 1.5 hours or about 1 hour. The Form VT1 may be isolated, preferably by any suitable process, such as decantation, filtration or by centrifuge, preferably by filtration. The Vericiguat form VT1 may be dried. The drying may be carried out under reduced pressure. The drying may be carried out at elevated temperature, preferably at a temperature of about 20° C. to about 80° C., about 30° C. to about 75° C., about 40° C. to about 65° C., or about 60° C., preferably under reduced pressure, and may be for any suitable time to remove the solvent(s), typically about 2 to about 30 hours, about 8 hours to about 25 hours, about 12 hours to about 20 hours, or about 16 hours. According to any embodiment of this process, after isolating the Vericiguat for VT1, preferably by filtration, the solid (which may be a wet solid following the isolating step, e.g. by filtration) may be optionally treated by slurrying in IPAc. Advantageously, this slurry step may promote the removal of DMAc from the Vericiguat Form VT1. The IPAc may be used in an amount of: about 4 ml to about 40 ml, about 8 ml to about 35 ml, about 10 ml to about 30 ml, about 15 ml to about 25 ml, or about 20 ml, per gram of Vericiguat. The mixture may be heated to a temperature of about 40° C. to about 90° C., about 50° C. to about 88° C., about 60° C. to about 85° C., or about 70° C. to about 80° C. The Vericiguat form VT1 may be slurried in the IPAc for a period of: about 0.5 hours to about 4 hours, about 0.6 hours to about 2 hours, or about 0.8 hours to about 1.5 hours or about 1 hour. The slurrying may be conducted at a temperature of about 50° C. to about 90° C., about 60° C. to about 88° C., about 70° C. to about 80° C., or about 73° C. to about 75° C. The mixture may be cooled to about ambient temperature. Vericiguat Form VT1 may be isolated, preferably by any suitable process, such as decantation, filtration or by centrifuge, preferably by filtration. The Vericiguat form VT1 may be dried. The drying may be carried out under reduced pressure. The drying may be carried out at elevated temperature, preferably at a temperature of about 20° C. to about 80° C., about 30° C. to about 75° C., about 40° C. to about 65° C., or about 60° C., preferably under reduced pressure, and may be for any suitable time to remove the solvent(s), typically about 2 to about 30 hours, about 8 hours to about 25 hours, about 12 hours to about 20 hours, or about 16 hours.

According to any aspect or embodiment of the processes for preparing a crystalline form of Vericiguat or salt (particularly Vericiguat hydrochloride), and the processes may further comprise combining the preparing a crystalline form of Vericiguat or salt (particularly Vericiguat hydrochloride) with at least one pharmaceutically acceptable excipient to prepare a pharmaceutical composition. Thus, according to any aspect or embodiment of the processes for preparing Vericiguat Form VT1 described herein, the processes may further comprise combining the Form VT1 with at least one pharmaceutically acceptable excipient to prepare a pharmaceutical composition.

Figure 10:
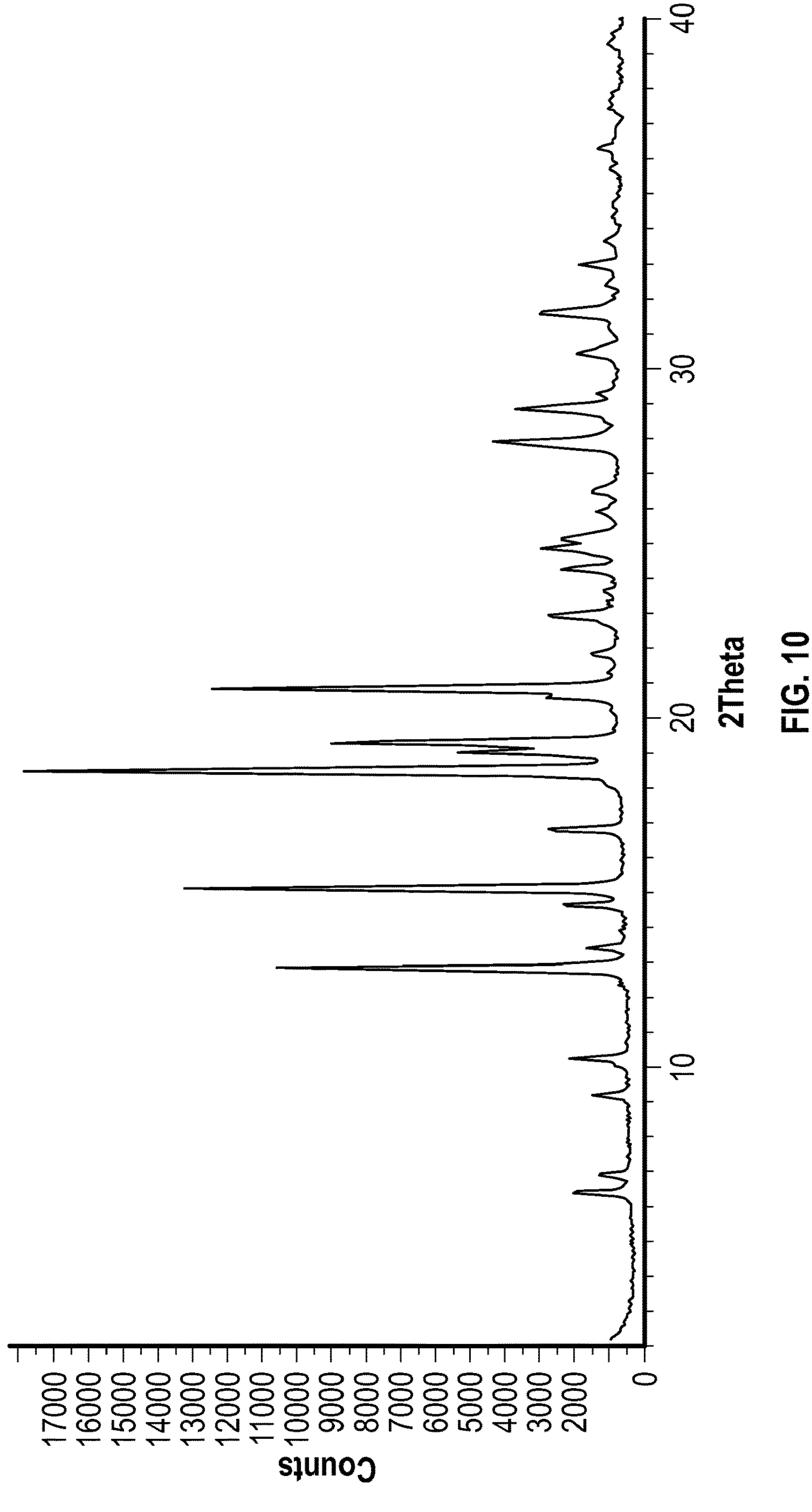
FIG. 10 shows a characteristic X-ray powder diffraction pattern (XRPD) of Vericiguat Form VT2.

The present disclosure includes a crystalline polymorph of Vericiguat, designated VT2. The crystalline Form VT2 of Vericiguat may be characterized by data selected from one or more of the following: an X-ray powder diffraction pattern substantially as depicted in FIG. 10; an X-ray powder diffraction pattern having peaks at 9.2, 15.1, 16.8, 20.8 and 27.9 degrees 2-theta±0.2 degrees 2-theta; and combinations of these data.

Crystalline Form VT2 of Vericiguat may be further characterized by an X-ray powder diffraction pattern having peaks at 9.2, 15.1, 16.8, 20.8 and 27.9 degrees 2-theta±0.2 degrees 2-theta, and also having any one, two, or three additional peaks selected from 6.9, 12.8, 14.6 and 18.5 degrees 2-theta±0.2 degrees 2-theta. Alternatively, crystalline Form VT2 of Vericiguat may be characterized by an X-ray powder diffraction pattern having peaks at 6.9, 9.2, 12.8, 14.6, 15.1, 16.8, 18.5, 20.8 and 27.9 degrees 2-theta±0.2 degrees 2-theta.

In one embodiment of the present disclosure, crystalline Form VT2 of Vericiguat is isolated.

Crystalline Form VT2 of Vericiguat may be DMF solvate form.

Crystalline Form VT2 of Vericiguat may be characterized by each of the above characteristics alone/or by all possible combinations, e.g., an XRPD pattern having peaks at 9.2, 15.1, 16.8, 20.8 and 27.9 degrees 2-theta±0.2 degrees 2-theta; an XRPD pattern as depicted in FIG. 10, and combinations thereof.

Figure 11:
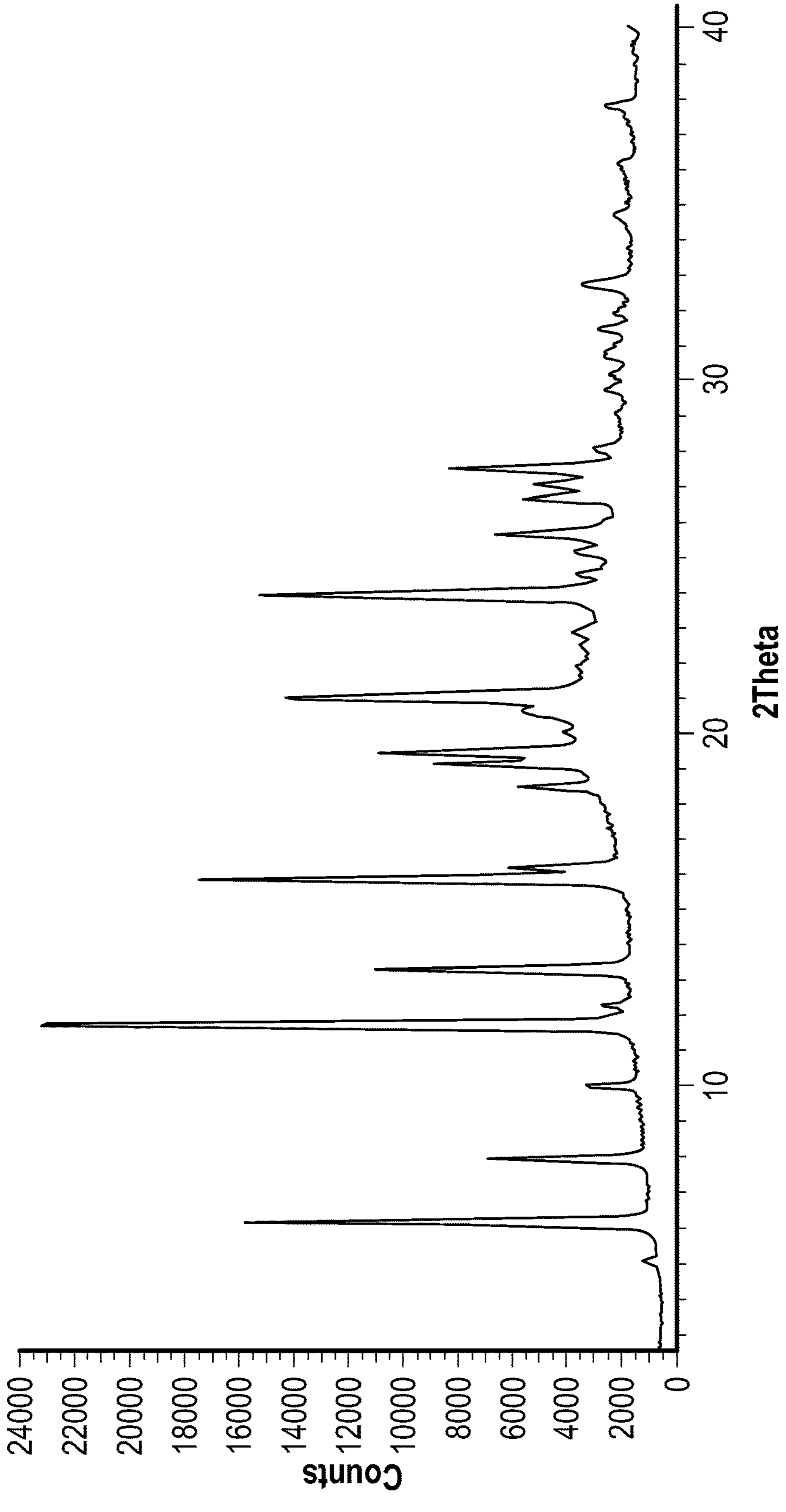
FIG. 11 shows a characteristic X-ray powder diffraction pattern (XRPD) of Vericiguat Form VT3.

The present disclosure includes a crystalline polymorph of Vericiguat, designated VT3. The crystalline Form VT3 of Vericiguat may be characterized by data selected from one or more of the following: an X-ray powder diffraction pattern substantially as depicted in FIG. 11; an X-ray powder diffraction pattern having peaks at 8.0, 11.8, 15.9, 21.0 and 23.9 degrees 2-theta±0.2 degrees 2-theta; and combinations of these data.

Crystalline Form VT3 of Vericiguat may be further characterized by an X-ray powder diffraction pattern having peaks at 8.0, 11.8, 15.9, 21.0 and 23.9 degrees 2-theta±0.2 degrees 2-theta, and also having any one, two, or three additional peaks selected from 6.2, 13.3, 19.5 and 25.6 degrees 2-theta±0.2 degrees 2-theta. Alternatively, crystalline Form VT3 of Vericiguat may be characterized by an X-ray powder diffraction pattern having peaks at 6.2, 8.0, 11.8, 13.3, 15.9, 19.5, 21.0, 25.6, and 23.9 degrees 2-theta±0.2 degrees 2-theta.

In one embodiment of the present disclosure, crystalline Form VT3 of Vericiguat is isolated.

Crystalline Form VT3 of Vericiguat may be Propylene glycol solvate form.

Crystalline Form VT3 of Vericiguat may be characterized by each of the above characteristics alone/or by all possible combinations, e.g., an XRPD pattern having peaks at 8.0, 11.8, 15.9, 21.0 and 23.9 degrees 2-theta±0.2 degrees 2-theta; an XRPD pattern as depicted in FIG. 11 and combinations thereof.

Figure 12:
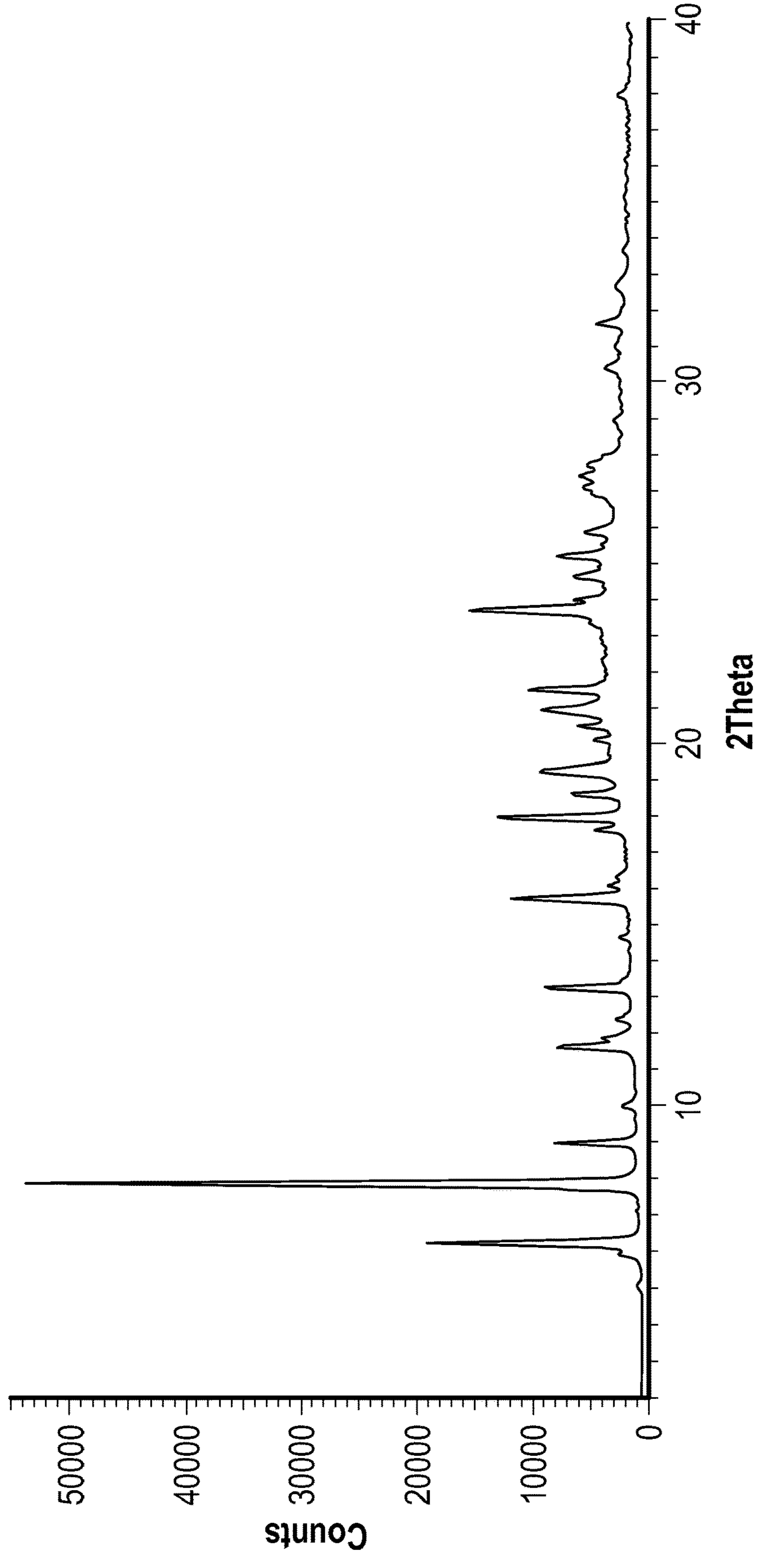
FIG. 12 shows a characteristic X-ray powder diffraction pattern (XRPD) of Vericiguat Form VT4.

The present disclosure includes a crystalline polymorph of Vericiguat, designated VT4. The crystalline Form VT4 of Vericiguat may be characterized by data selected from one or more of the following: an X-ray powder diffraction pattern substantially as depicted in FIG. 12; an X-ray powder diffraction pattern having peaks at 7.8, 8.9, 17.9, 21.5 and 23.7 degrees 2-theta±0.2 degrees 2-theta; and combinations of these data.

Crystalline Form VT4 of Vericiguat may be further characterized by an X-ray powder diffraction pattern having peaks at 7.8, 8.9, 17.9, 21.5 and 23.7 degrees 2-theta±0.2 degrees 2-theta, and also having any one, two, or three additional peaks selected from 13.2, 15.7, 18.6 and 19.2 degrees 2-theta±0.2 degrees 2-theta. Alternatively, crystalline Form VT4 of Vericiguat may be characterized by an X-ray powder diffraction pattern having peaks at 7.8, 8.9, 13.2, 15.7, 17.9, 18.6, 19.2, 21.5 and 23.7 degrees 2-theta±0.2 degrees 2-theta.

In one embodiment of the present disclosure, crystalline Form VT4 of Vericiguat is isolated.

Crystalline Form VT4 of Vericiguat may be Ethylene glycol solvate form.

Crystalline Form VT4 of Vericiguat may be characterized by each of the above characteristics alone/or by all possible combinations, e.g., an XRPD pattern having peaks at 7.8, 8.9, 17.9, 21.5 and 23.7 degrees 2-theta±0.2 degrees 2-theta; an XRPD pattern as depicted in FIG. 12 and combinations thereof.

Figure 13:
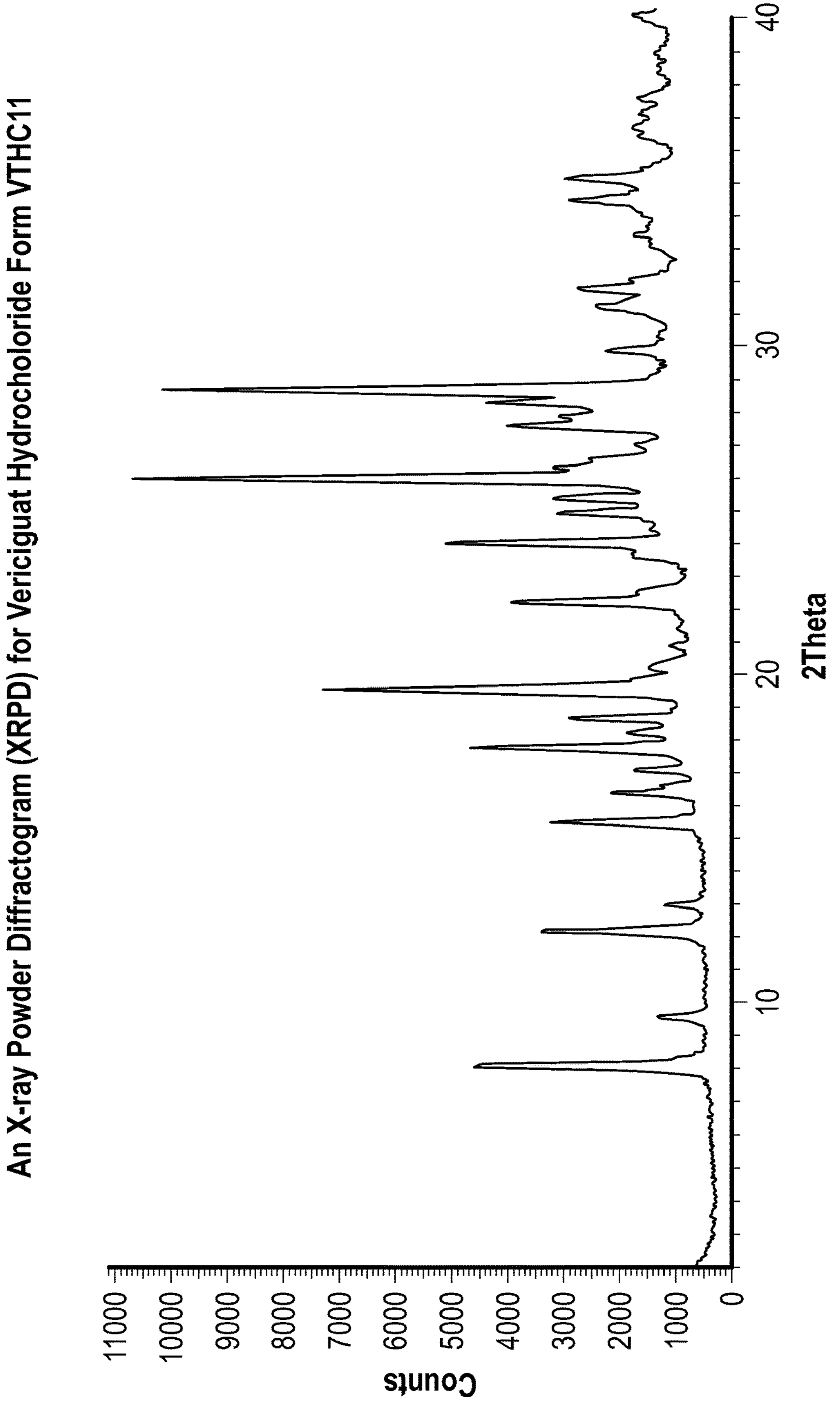
FIG. 13 shows a characteristic X-ray powder diffraction pattern (XRPD) of Vericiguat hydrochloride Form VTHCl1.

The present disclosure includes a crystalline polymorph of Vericiguat hydrochloride, designated VTHCl1. The crystalline Form VTHCl1 of Vericiguat hydrochloride may be characterized by data selected from one or more of the following: an X-ray powder diffraction pattern substantially as depicted in FIG. 13; an X-ray powder diffraction pattern having peaks at 8.5, 10.0, 12.6, 22.4 and 26.2 degrees 2-theta±0.2 degrees 2-theta; and combinations of these data.

Crystalline Form VTHCl1 of Vericiguat hydrochloride may be further characterized by an X-ray powder diffraction pattern having peaks at 8.5, 10.0, 12.6, 22.4 and 26.2 degrees 2-theta±0.2 degrees 2-theta, and also having any one, two, three or four additional peaks selected from 18.1, 19.8, 24.2 and 28.8 degrees 2-theta±0.2 degrees 2-theta. Alternatively, crystalline Form VTHCl1 of Vericiguat hydrochloride may be characterized by an X-ray powder diffraction pattern having peaks at 8.5, 10.0, 12.6, 18.1, 19.8, 22.4, 24.2, 26.2, and 28.8 degrees 2-theta±0.2 degrees 2-theta.

In one embodiment of the present disclosure, crystalline Form VTHCl1 of Vericiguat hydrochloride is isolated.

In one embodiment of the present disclosure, crystalline Form VTHCl1 of Vericiguat hydrochloride has melting point of 233.6° C. measured by Differential scanning calorimeter.

Crystalline Form VTHCl1 of Vericiguat hydrochloride may be hydrate form.

Crystalline Form VTHCl1 of Vericiguat hydrochloride may be characterized by each of the above characteristics alone/or by all possible combinations, e.g., an XRPD pattern having peaks at 8.5, 10.0, 12.6, 22.4 and 26.2 degrees 2-theta±0.2 degrees 2-theta; an XRPD pattern as depicted in FIG. 13, and combinations thereof.

Figure 14:
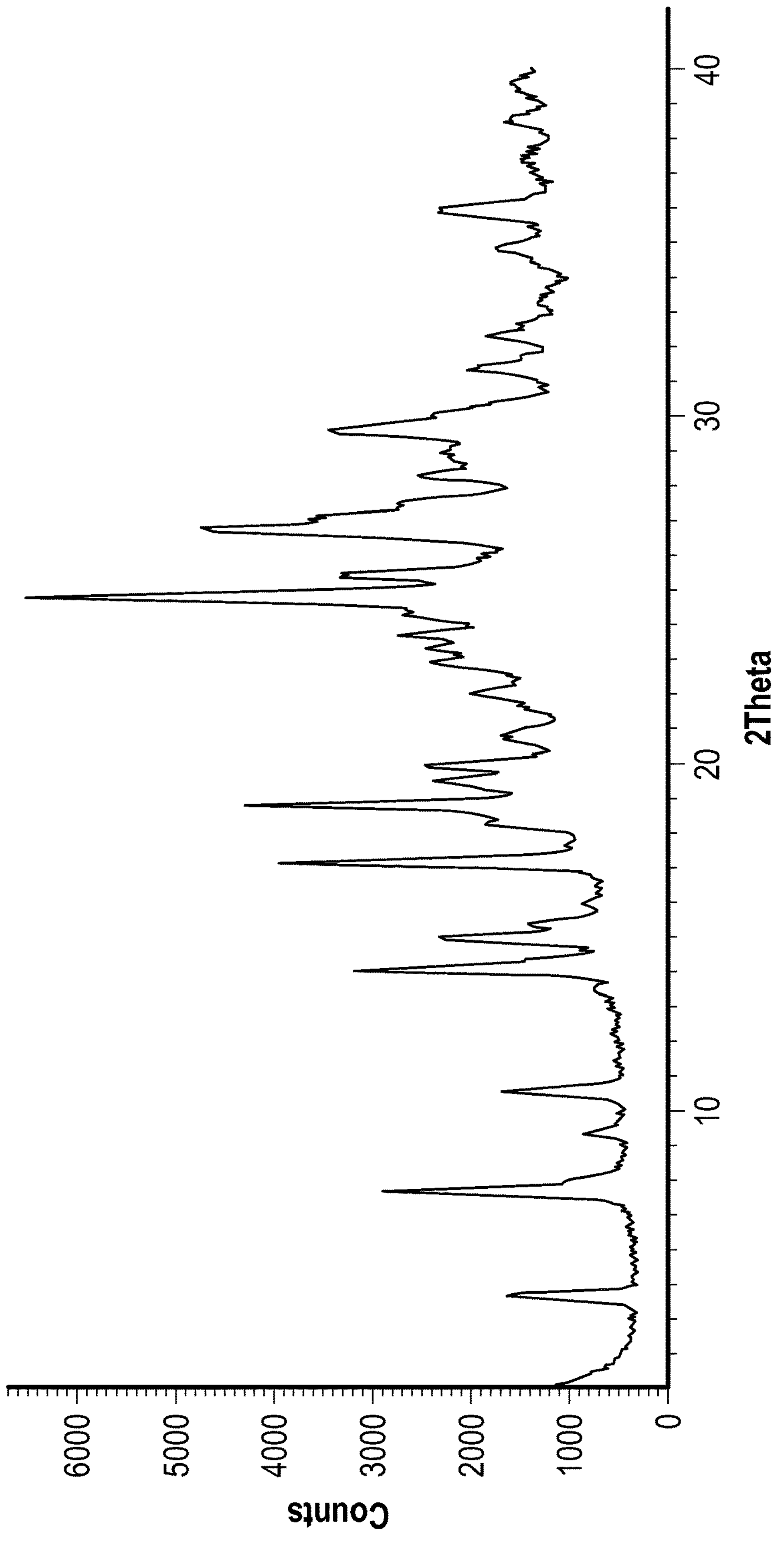
FIG. 14 shows a characteristic X-ray powder diffraction pattern (XRPD) of Vericiguat hydrochloride Form VTHCl2.

The present disclosure includes a crystalline polymorph of Vericiguat hydrochloride, designated VTHCl2. The crystalline Form VTHCl2 of Vericiguat hydrochloride may be characterized by data selected from one or more of the following: an X-ray powder diffraction pattern substantially as depicted in FIG. 14; an X-ray powder diffraction pattern having peaks at 4.7, 7.7, 10.6, 14.0 and 15.0 degrees 2-theta±0.2 degrees 2-theta; and combinations of these data.

Crystalline Form VTHCl2 of Vericiguat hydrochloride may be further characterized by an X-ray powder diffraction pattern having peaks at 4.7, 7.7, 10.6, 14.0 and 15.0 degrees 2-theta±0.2 degrees 2-theta, and also having any one, two, three or four additional peaks selected from 17.2, 18.8, 24.8 and 26.8 degrees 2-theta±0.2 degrees 2-theta. Alternatively, crystalline Form VTHCl2 of Vericiguat hydrochloride may be characterized by an X-ray powder diffraction pattern having peaks at 4.7, 7.7, 10.6, 14.0, 15.0, 17.2, 18.8, 24.8, and 26.8 degrees 2-theta±0.2 degrees 2-theta.

In one embodiment of the present disclosure, crystalline Form VTHCl2 of Vericiguat hydrochloride is isolated.

Crystalline Form VTHCl2 of Vericiguat hydrochloride may be anhydrous form.

In one embodiment of the present disclosure, crystalline Form VTHCl2 of Vericiguat hydrochloride has melting point of 234.7 measured by Differential scanning calorimeter. Accordingly, crystalline Form VTHCl2 of Vericiguat hydrochloride maybe further characterized by having a DSC melting point of 234.7° C.

Crystalline Form VTHCl2 of Vericiguat hydrochloride may be characterized by each of the above characteristics alone/or by all possible combinations, e.g., an XRPD pattern having peaks at 4.7, 7.7, 10.6, 14.0 and 15.0 degrees 2-theta±0.2 degrees 2-theta; an XRPD pattern as depicted in FIG. 14, and combinations thereof. In any aspect or embodiment of the present disclosure, any of the solid state forms of Vericiguat or salts of Vericiguat, particularly Vericiguat hydrochloride may be polymorphically pure or may be substantially free of any other solid state forms of the subject Vericiguat or salts of Vericiguat, particularly Vericiguat hydrochloride (for example a crystalline Form V1 of Vericiguat which is polymorphically pure, may be substantially free of any other solid state forms of Vericiguat; or a crystalline Form VTHCl1 of Vericiguat hydrochloride which is polymorphically pure, may be substantially free of other solid state forms of Vericiguat hydrochloride). In particular, in any aspect or embodiment of the present disclosure, any of the solid state forms of Vericiguat or salts of Vericiguat, particularly Vericiguat hydrochloride described in any aspect or embodiment disclosed herein, may contain: about 20% (w/w) or less, about 10% (w/w) or less, about 5% (w/w) or less, about 2% (w/w) or less, about 1% (w/w) or less, about 0.5% (w/w) or less, about 0.2% (w/w) or less, about 0.1% (w/w) or less, or about 0%, of any other solid state forms of the subject compound (i.e. Vericiguat or salts of Vericiguat, particularly Vericiguat hydrochloride, respectively), preferably as measured by XRPD. Thus, any of the disclosed crystalline forms of Vericiguat or salts of Vericiguat, particularly Vericiguat hydrochloride, described herein may be substantially free of any other solid state forms of the subject Vericiguat or salts of Vericiguat, particularly Vericiguat hydrochloride, respectively, and may contain greater than about 80% (w/w), greater than about 90% (w/w), greater than about 95% (w/w), greater than about 98% (w/w), greater than about 99% (w/w), or about 100% of the subject solid state form of Vericiguat or salts of Vericiguat, particularly Vericiguat hydrochloride.

In any aspect or embodiment of the present disclosure, any of the solid state forms of Vericiguat or salts of Vericiguat, particularly Vericiguat hydrochloride, may be a purified form. In particular, in any aspect or embodiment of the present disclosure, any of solid state forms of Vericiguat or salts of Vericiguat, particularly Vericiguat hydrochloride, may be substantially free of impurities as well as artifacts of the preparative process. Preferably, the "purified" form may have a purity of at least 95%, 96%, 97%, 98%, 98.5%, 99%, 99.2%, 99.4%, 99.6%, 99.8% or 99.9% by weight, preferably as measured by HPLC.

The present disclosure also provides solid state forms of Vericiguat of the present disclosure for use in the preparation of other solid state forms of Vericiguat, Vericiguat salts, particularly Vericiguat hydrochloride and their solid state forms. The present disclosure further encompasses processes for preparing other solid state forms of Vericiguat, particularly Vericiguat hydrochloride and their solid state forms thereof. The process can comprise preparing any one or a combination of the above described solid state form of Vericiguat and salts of Vericiguat, particularly Vericiguat hydrochloride by the process of the present disclosure, and converting it to other solid state forms of Vericiguat, Vericiguat salt and solid state forms thereof.

In another embodiment, the present disclosure encompasses the above described solid state form of Vericiguat for use in the preparation of pharmaceutical compositions and/or formulations, optionally for the treatment of chronic heart failure.

In another embodiment, the present disclosure encompasses the use of the above described solid state form of Vericiguat for the preparation of pharmaceutical compositions and/or formulations. The present disclosure also provides the solid state form of Vericiguat of the present disclosure for use in the preparation of pharmaceutical compositions and/or formulations.

The present disclosure further provides pharmaceutical compositions comprising any one or a mixture of the solid state form of Vericiguat, according to the present disclosure.

In yet another embodiment, the present disclosure encompasses pharmaceutical formulations comprising any one or a mixture of the solid state form of Vericiguat and at least one pharmaceutically acceptable excipient.

Pharmaceutical formulations of the present invention contain any one or a combination of the crystalline forms of Vericiguat of the present disclosure. In addition to the active ingredient, the pharmaceutical formulations of the present disclosure can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present invention include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present disclosure, the active ingredient and any other solid excipients may be dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present disclosure can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present disclosure is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, such as a powdered or granulated solid composition of the invention, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, but they are not subjected to a final tableting step.

In embodiments, a pharmaceutical formulation of Vericiguat is formulated for administration to a mammal, such as a human. Vericiguat can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The present disclosure encompasses processes to prepare said formulations of Vericiguat comprising combining any one or a mixture of the solid state form of Vericiguat and at least one pharmaceutically acceptable excipient.

The solid state forms of Vericiguat as defined herein, as well as the pharmaceutical compositions or formulations thereof, at least can be used as medicaments, particularly for the treatment of for treating chronic heart failure.

The present disclosure also provides methods of treating chronic heart failure; comprising administering a therapeutically effective amount of any one or a mixture of the solid state form of Vericiguat of the present disclosure, or at least one of the above pharmaceutical compositions or formulations, to a subject suffering from chronic heart failure or otherwise in need of the treatment.

The present disclosure also provides use of the solid state form of Vericiguat of the present disclosure, or at least one of the above pharmaceutical compositions or formulations for the manufacture of a medicament for treating chronic heart failure.

Having described the disclosure with reference to certain preferred embodiments, other embodiments will become apparent to one skilled in the art from consideration of the specification. The disclosure is further illustrated by reference to the following examples describing in detail the preparation of the composition and methods of use of the disclosure. It will be apparent to those skilled in the art that many modifications, both to materials and methods, may be practiced without departing from the scope of the disclosure.

Analytical Methods

X-Ray Powder Diffraction Method for Form V1, V2, V3, V4, V5 and V6:

XRPD analysis was performed on ARL (SCINTAG) powder X-Ray diffractometer model X'TRA equipped with a solid state detector. Copper radiation of 1.5418 Å was used. Scanning parameters: range: 2-40 degrees two-theta; scan mode: continuous scan; step size: 0.05°, and a rate of 3 deg/min.

Powder X-Ray Diffraction ("XRPD") Method for Form VT1, VT2, VT3 VT4, VHCl1 and VHCl2

X-ray diffraction was performed on X-Ray powder diffractometer: Bruker D8 Advance; CuKα radiation (λ=1.5418 Å); Lynx eye detector; laboratory temperature 22-25° C.; PMMA specimen holder ring with silicon low background. Prior to analysis, the samples were gently ground by means of mortar and pestle in order to obtain a fine powder. The ground sample was adjusted into a cavity of the sample holder and the surface of the sample was smoothed by means of a cover glass.

Measurement Parameters:

Scan range: 2-40 degrees 2-theta;

Scan mode: continuous;

Step size: 0.05 degrees;

Time per step: 0.5 s;

Sample spin: 30 rpm;

Sample holder: PMMA specimen holder ring with silicon low background.

All X-Ray Powder Diffraction peak values are calibrated with regard to standard silicon spiking in the sample.

SSNMR Method:

Solid-state NMR spectra were measured at 11.7 T using a Bruker Avance III HD 500 US/WB NMR spectrometer (Karlsruhe, Germany, 2013) with 3.2 mm probehead. The 13C CP/MAS NMR spectra employing cross-polarization were acquired using the standard pulse scheme at spinning frequency of 15 kHz and a room temperature (300 K). The recycle delay was 8 s and the cross-polarization contact time was 2 ms, the 13C scale was referenced to α-glycine (176.03 ppm for 13C). Frictional heating of the spinning samples was offset by active cooling, and the temperature calibration was performed with Pb(NO3)2. The NMR spectrometer was completely calibrated and all experimental parameters were carefully optimized prior the investigation. Magic angle was set using KBr during standard optimization procedure and homogeneity of magnetic field was optimized using adamantane sample (resulting line-width at half-height Δυ½ was less than 3.5 Hz at 250 ms of acquisition time).

EXAMPLES

Preparation of Starting Material

Vericiguat can be prepared by any process disclosed in the literature, for example WO 2011/147809 and WO2013/076168.

Vericiguat (polymorph I) can be prepared according to methods known from the literature, for example U.S. Pat. No. 9,604,948.

2-(5-fluoro-1-(2-fluorobenzyl)-1H-pyrazolo[3,4-b]pyridin-3-yl)pyrimidine-4,5,6-triamine can be prepared according to methods known from the literature, for example U.S. Pat. No. 8,420,656.

Example 1: Preparation of Crystalline Vericiguat Form V1

Step 1: Purification of Vericiguat

Figure 7:
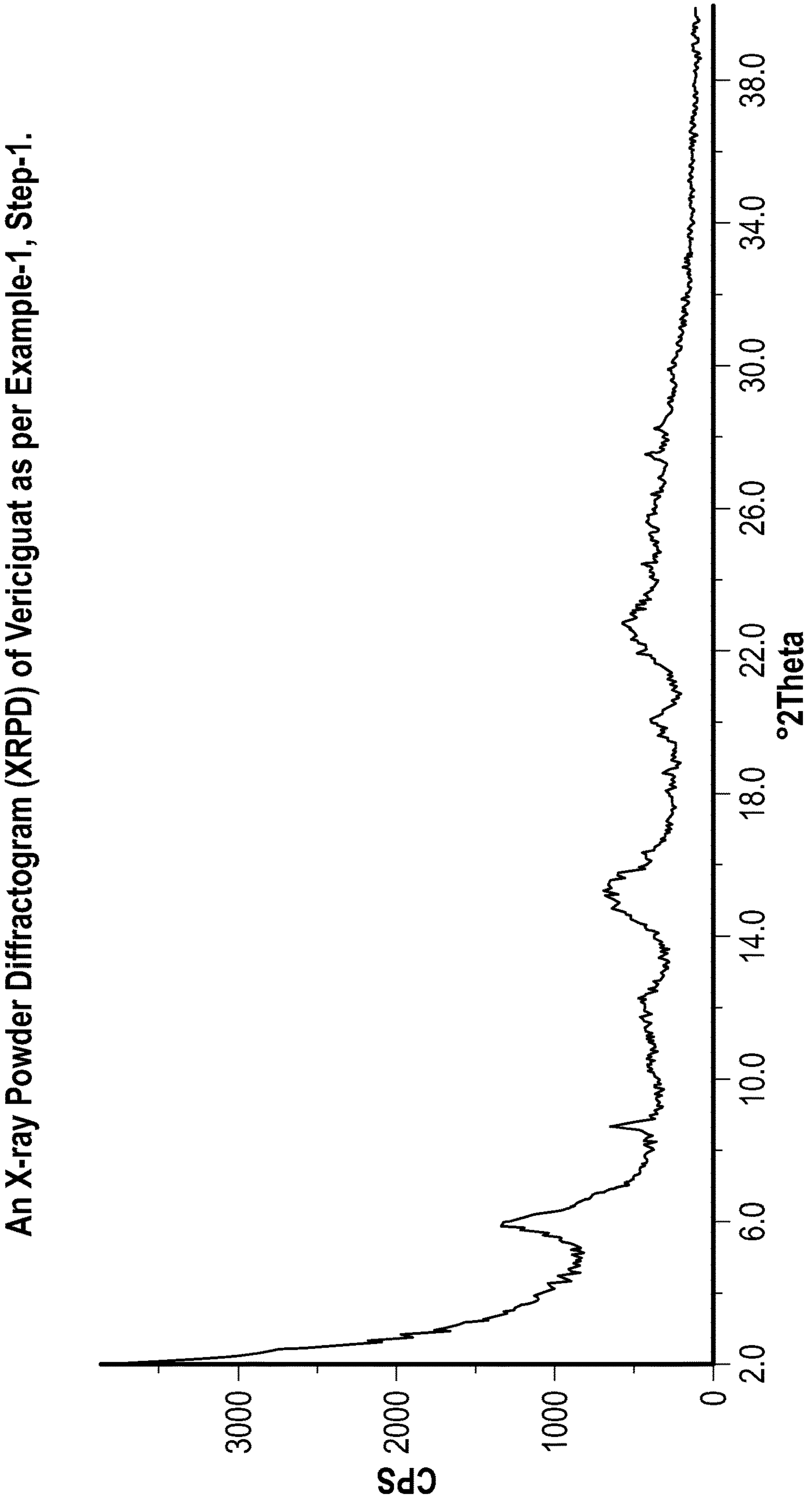
FIG. 7 shows an X-ray powder diffractogram (XRPD) of Vericiguat as per Example-1, step-1.

Vericiguat (5 g, less than about 80% purity; by Thin Layer Chromatography) and 2,2,2-trifluoroethanol (250 ml, 50 V) were added to a 1 L reactor at room temperature and a slurry was formed. The slurry was heated to temperature of about 72° C. and was stirred at this temperature over a period of 1.5 hour. Next, the slurry was left to cool spontaneously to temperature of about 25° C. and was stirred at this temperature for about 19 hours. The slurry was vacuum filtered and washed with 2,2,2-trifluoroethanol (1×100 ml, 20 Volume). The isolated wet solid was loaded to the 1 L reactor with 2-propanol (900 ml, 180 Volume) and a slurry was formed. The obtained slurry was heated to temperature of about 80° C. until a clear light brown solution was obtained. This clear solution was hot filtered by vacuum. The obtained clear solution was transferred to the reactor followed by addition of active carbon (5 g) to this solution. After stirring at temperature of about 80° C. over a period of 1 hour, the active carbon was removed by hot filtration under vacuum to give off-white solution, which was evaporated under reduce pressure to provide Vericiguat (purity: not less than 98% by TLC; about 60% yield) analyzed by XRPD, and PXRD pattern is shown in FIG. 7.

Step 2: Preparation of Vericiguat Form V1

Vericiguat (2.37 g obtained in from Step 1) was dissolved in dimethyl sulphoxide (60 g at room temperature and a solution was formed. The obtained solution was mechanically filtered (0.2 micron). The obtained clear yellow solution was lyophilized upon −45° C. to 30° C. to obtain a solid. The obtained solid was analyzed by XRPD, Vericiguat Form V1 was obtained, and PXRD pattern is shown in FIG. 1.

Example 2: Preparation of Crystalline Vericiguat Form V2

1,2-Dioxolane (0.75 ml, 25 Volume) was added to Vericiguat form V1 (0.03 g, 0.07 mmol) at room temperature and a slurry was formed. The slurry was stirred and heated to temperature of about 75° C. and a cloudy solution formed, which was mechanically hot filtered under filter disk. The obtained clear filtrate was heated again to temperature of about 75° C. and methyl ethyl ketone (0.75 ml, 25 Volume) was added in one portion to the hot stirred solution. The solution was stirred at temperature of about 75° C. over a period of 30 minutes. Then, the solution was left to spontaneously cool to room temperature and was stirred at this temperature over a period of about 18 hours, and precipitation occurred. The obtained precipitant was filtered by centrifuge. The obtained solid was analyzed by XRPD, Vericiguat Form V2 was obtained, and PXRD pattern is shown in FIG. 2.

Example 3: Preparation of Crystalline Vericiguat Form V3

Acetic acid (0.75 ml, 15 V) was added to Vericiguat form V1 (0.05 g, 0.12 mmol) at room temperature and a slurry was formed. The obtained slurry was stirred at room temperature over a period of about 10 minutes and complete dissolution occurred. After stirring at room temperature over a period of 5 minutes, precipitation was observed. This obtained precipitant was stirred at room temperature over a period of about 18 hours, filtered by centrifuge, washed with water (0.5 ml×2) and dried in a vacuum oven at temperature of about 45° C. for about 18 hours. The isolated solid was characterized by X-ray powder diffraction, Vericiguat Form V3 was obtained, and PXRD pattern is shown in FIG. 3.

Example 4: Preparation of Crystalline Vericiguat Form V4

Propionic acid (0.6 ml, 3 V) was added to Vericiguat form V1 (0.2 g, 0.47 mmol) at room temperature and a slurry was formed. The obtained slurry was stirred at room temperature and a cloudy solution formed. After stirring at room temperature over a period of 15 minutes, precipitation was observed. This obtained precipitant was stirred at room temperature over a period of about 2 hours. Then, additional portion of propionic acid (2 ml, 10 V) was added to the precipitant. The obtained slurry was stirred at room temperature for about 18 hours followed by vacuum filtration and drying in a vacuum oven at temperature of about 40° C. for about 2.5 hours. The obtained solid was analyzed by XRPD, Vericiguat Form V4 was obtained, and PXRD pattern is shown in FIG. 4.

Example 5: Preparation of Crystalline Vericiguat Form V5

Formic acid (0.2 ml, 6.7 Volume) was added to Vericiguat form V1 (0.03 g, 0.07 mmol) at room temperature and a clear solution was formed. The solution was maintained in open vessel at room temperature over a period of about 48 hours and a solid was obtained. The obtained solid was analyzed by XRPD, Vericiguat Form V5 was obtained, and PXRD pattern is shown in FIG. 5.

Example 6: Preparation of Crystalline Vericiguat Form V2

1,2-Dioxolane (12.5 ml, 25 Volume) was added to Vericiguat form V1 (0.5 g, 1.16 mmol) at room temperature and a slurry was formed. The slurry was stirred and heated to temperature of about 75° C. and a cloudy solution formed, which was mechanically hot filtered under filter disk. The obtained clear filtrate was heated again to temperature of about 75° C. and methyl ethyl ketone (12.5 ml, 25 Volume) was added in one portion to the hot stirred solution. The solution was stirred at temperature of about 75° C. over a period of 30 minutes. Then, the solution was left to spontaneously cool to room temperature and then cool to 4° C. The solution was stirred at this temperature over a period of about 18 hours, and precipitation occurred. The obtained precipitant was filtered by centrifuge to afford wet solid and dried in vacuum oven at 40° C. over a period of 18 hours. The obtained solid was analyzed by XRPD, Vericiguat Form V2 was obtained.

Example 7: Preparation of Crystalline Vericiguat Form V2

2-ethoxy ethanol (cellosolve) (43 ml, 43 Volume) was added to Vericiguat form V1 (1 g, 2.32 mmol) at room temperature and a slurry was formed. The slurry was magnetically stirred and heated to about 100° C. over a period of 15 minutes to obtain complete dissolution follows by mechanically filtration using filter disk. Then, the solution was left to spontaneously cool to room temperature and was stirred at this temperature over a period of about 72 hours, and precipitation occurred. The solid was then filtered by centrifuge to afford wet solid and dried in vacuum oven at 50° C. over a period of 18 hours. The obtained solid was analyzed by XRPD, Vericiguat Form V2 was obtained.

Example 8: Preparation of Crystalline Vericiguat Form V2

2-ethoxy ethanol (cellosolve) (1.05 ml, 35 Volume) was added to Vericiguat form V1 (0.03 g, 0.07 mmol) at room temperature and a slurry was formed. The slurry was magnetically stirred and heated to about 100° C. over a period of 15 minutes to obtain complete dissolution follows by mechanically filtration using filter disk. Next, the MIBK (methyl isobutyl ketone) as anti-solvent (1.05 ml) was added drop-wise to the stirred clear solution at about 100° C. Then, the solution was left to spontaneously cool to room temperature and stirred at room temperature over a period of 24 hours, and precipitation occurred. The obtained precipitant was filtered by centrifuge. The obtained solid was analyzed by XRPD, Vericiguat Form V2 was obtained.

Example 9: Preparation of Crystalline Vericiguat Form V2

2-ethoxy ethanol (cellosolve) (1.05 ml, 35 Volume) was added to Vericiguat form V1 (0.03 g, 0.07 mmol) at room temperature and a slurry was formed. The slurry was magnetically stirred and heated to 100° C. over a period of 15 minutes to obtain complete dissolution follows by mechanically filtration using filter disk. Next, the isopropyl alcohol as anti-solvent (1.05 ml) was added drop-wise to the stirred clear solution at about 100° C. Then, the solution was left to spontaneously cool to room temperature and stirred at room temperature over a period of 24 hours, and precipitation occurred. The obtained precipitant was filtered by centrifuge. The obtained solid was analyzed by XRPD, Vericiguat Form V2 was obtained.

Example 10: Preparation of Crystalline Vericiguat Form V6

Propionic acid (6 ml, 15 Volume) was added to Vericiguat (prepared according to example 1, step 1) (0.4 g, 0.93 mmol) at room temperature and a slurry was formed. The slurry was stirred and heated to temperature of about 40° C. and was stirred at this temperature over a period of about 18 hours. The solid was then filtered by centrifuge to afford wet solid and dried in vacuum oven at 45° C. over a period of 16 hours. The obtained solid was analyzed by XRPD, Vericiguat Form V6 was obtained, and PXRD pattern is shown in FIG. 6.

Example 11: Preparation of Vericiguat Form VT1

Vericiguat (0.5 g) was taken in a 50 mL RB flask and was dissolved in 25 mL of 1,4-Dioxane at temperature of about 100° C. The clear solution was filtered with 0.45μ filter at temperature of about 100° C. and added to 75 mL of precooled (0° C.) Isopropyl acetate and was stirred at temperature of about 0° C. for period of about 2 hours. The obtained solid was filtered at temperature of about 0° C. and suction dried at temperature of about 25° C. for period of about 30 minutes. Further the solid was dried under vacuum at temperature of about 60° C. for period of about 2 hours. The obtained solid was analyzed by XRPD. Vericiguat Form VT1 was obtained. An XRPD pattern is shown in FIG. 8.

Example 12: Preparation of Vericiguat Form VT1

Vericiguat (0.5 g) was taken in a 50 mL RB flask and was dissolved in 25 mL of 1,4-Dioxane at temperature of about 100° C. The clear solution was filtered with 0.45μ filter at temperature of about 100° C. and added to 75 mL of precooled (0° C.) n-butyl acetate and was stirred at temperature of about 0° C. for period of about 2 hours. The obtained solid was filtered at temperature of about 0° C. and suction dried at temperature of about 25° C. for period of about 30 minutes. Further the solid was dried under vacuum at temperature of about 60° C. for period of about 2 hours. The obtained solid analyzed by XRPD. Vericiguat Form VT1 was obtained.

Example 13: Preparation of Vericiguat Form VT1

Vericiguat (0.5 g) was taken in a 500 mL RB flask and was dissolved in 250 ml of THF at temperature of about 60° C. The clear solution was filtered at temperature of about 60° C. and subjected to distillation under reduced pressure at temperature of about 60° C. The Solid was obtained in 15 minutes. The obtained solid was cooled to temperature of about 20° C. to about 25° C. and was washed with 50 mL of MTBE and filtered at temperature of about 20° C. to about 25° C. The obtained solid analyzed by XRPD. Vericiguat Form VT1 was obtained.

Example 14: Preparation of Vericiguat Form VT1

Vericiguat (5.0 g) was charged in the RB flask, 40 mL of DMAc was added to it and was heated to temperature of about 50° C. to about 60° C. to obtain clear solution and filtered it through 0.45 micron and washed with 5 mL DMAc. 200 mL of IPAc was charged at temperature of about 20° C. to about 30° C. in another RB flask and dropwise DMAc solution of Vericiguat was added into it at temperature of about 25° C. to about 27° C. in period of about 15 minutes to about 30 minutes with stirring and stirring was maintained at temperature of about 25° C. to about 27° C. for period of about 1 hour. The obtained solid was filtered and washed with 10 mL of IPAc twice. The wet solid was further charged in 150 mL RB flask and 100 mL of IPAc was added to it and heated to temperature of about 70° C. to about 80° C. and stirred for period of 1 hour at temperature of about 73° C. to about 75° C. then allowed to cool to temperature of about 20° C. to about 30° C. The Solid was filtered and washed with 10 mL of IPAc twice. The obtained solid was dried under Vacuum tray drier at temperature of about 60° C. for period of about 16 hours and was analyzed by XRPD. Vericiguat Form VT1 was obtained. An XRPD pattern is shown in FIG. 9.

Example 15: Preparation of Vericiguat Form VT2

Vericiguat (1.0 g) was taken in a 250 mL round bottom flask and was dissolved in 80 mL of N, N-Dimethyl Formamide at temperature of about 70° C. The clear solution was filtered with 0.45μ filter at temperature of about 70° C. 200 mL of precooled (at temperature of about 0° C.) n-heptane was added at temperature of about 70° C. The solid obtained was stirred for period of about 10 minutes and cooled to temperature of about 25° C. in period of about 1 hour. The solid was filtered after period of about 2 hours and dried under suction at temperature of about 25° C. for period of about 30 minutes. Further the solid was dried under vacuum at temperature of about 60° C. for period of about 2 hours. The obtained solid was analyzed by XRPD. Vericiguat Form VT2 was obtained An XRPD pattern is shown in FIG. 10.

Example 16: Preparation of Vericiguat Form VT3

Vericiguat Form VT1 (0.05 g) was taken in a 2 mL vial and was suspended in 2 mL of Propylene glycol and stirred at temperature of about 60° C. for period of about 2 hours. The suspension was cooled to temperature of about 25° C. in period of about 1 hour and filtered and dried suction at temperature of about 25° C. for period of about 30 minutes. Further the solid was dried under vacuum at temperature of about 60° C. for period of about 2 hours. The obtained solid was analyzed by XRPD. Vericiguat Form VT3 was obtained An XRPD pattern is shown in FIG. 11.

Example 17: Preparation of Vericiguat Form VT4

Vericiguat Form VT1 (0.05 g) was taken in a 2 mL vial and was suspended in 2 mL of Ethylene glycol and stirred at temperature of about 60° C. for period of about 2 hours. The suspension was cooled to temperature of about 25° C. in period of about 1 hour and was filtered and suction dried at temperature of about 25° C. for period of about 30 minutes. Further the solid was dried under vacuum at temperature of about 60° C. for period of about 2 hours. The obtained solid was analyzed by XRPD. Vericiguat Form VT4 was obtained. An XRPD pattern is shown in FIG. 12.

Example 18: Preparation of Vericiguat Hydrochloride Form VTHCl1

Vericiguat (polymorph I) (0.1 g) was taken in a 100 mL RB flask and was suspended in 100 mL of pH 1.2 HCl buffer at 37° C. After 24 hours, the solid was filtered and dried suction at temperature of about 25° C. for period of about 30 minutes. The obtained solid analyzed by XRPD. Vericiguat Hydrochloride Form VTHCl1 was obtained. An XRPD pattern is shown in FIG. 13.

Example 19: Preparation of Vericiguat Hydrochloride Form VTHCl2

Vericiguat (polymorph I) (0.1 g) was taken in a 100 mL RB flask and was suspended in 100 mL of pH 1.2 HCl buffer at temperature of about 37° C. After 24 hours, the solid was filtered and dried under suction at temperature of about 25° C. for period of about 30 minutes. Further the solid was dried under vacuum at temperature of about 60° C. for period of about 5 hours. The obtained solid was analyzed by XRPD. Vericiguat Hydrochloride Form VTHCl2 was obtained. An XRPD pattern is shown in FIG. 14.

Example 20: Preparation of Vericiguat Hydrochloride 2-(5-fluoro-1-(2-fluorobenzyl)-1H-pyrazolo[3,4-b]pyridin-3-yl)pyrimidine-4,5,6-triamine (5.0 gm, 0.0136 mol) was charged in DMF (4 Vol) and pyridine (2 Vol). Reaction mass was cooled to temperature of about 0° C. to about 5° C., dropwise methyl chloroformate (1.41 g, 0.015 mol) was added at temperature of about 0° C. to about 5° C. and stirred for period of about 30 minutes to about 60 minutes. After completion of reaction, the temperature of reaction mass was raised to temperature of about 20° C. to about 30° C., charcoal (5%) was charged and stirred for period of about 60 minutes, filtered through hyflo bed and washed with DMF (1 Vol) at temperature of about 20° C. to about 30° C. The filtrate was charged in another RBF, slowly ethyl acetate (200 ml) was added at 20-30° C., Stirred, filtered and washed with ethyl acetate to get Vericiguat hydrochloride. HPLC purity: 99.71%

Example 21: Preparation of Vericiguat Hydrochloride 2-(5-fluoro-1-(2-fluorobenzyl)-1H-pyrazolo[3,4-b]pyridin-3-yl)pyrimidine-4,5,6-triamine (20.0 gm, 0.054 mol) was charged in DMF (4 Vol) and pyridine (2 Vol). Reaction mass was cooled to temperature of about 0° C. to about 5° C., dropwise methyl chloroformate (5.64 g, 0.060 mol) was added at temperature of about 0° C. to about 5° C. and stirred for period of about 30 minutes to about 60 minutes. After completion of reaction, activated charcoal (5%) was added and stirred for period of about 60 minutes, filtered through hyflo bed and washed with DMF (1 Vol). Into filtrate, ethyl acetate (40 Vol) was added in the period of about 60 minutes to about 90 minutes at temperature of about 20° C. to about 30° C., filtered and washed with ethyl acetate to get Vericiguat hydrochloride. HPLC purity 99.67%

Example 22: Preparation of Vericiguat

Vericiguat hydrochloride (6 gm) salt was added to 3.5% aqueous sodium carbonate solution (10 Vol), stirred for period of about 30 minutes at temperature of about 20° C. to about 30° C., filtered, washed with water and dried under vacuum at temperature of about 55° C. to about 60° C. to get Vericiguat (4.8 gm). HPLC purity 99.7%

Example 23: Preparation of Vericiguat

Vericiguat hydrochloride (1.5 gm) was dissolved in methanol at temperature of about 20° C. to about 30° C. Activated carbon (0.6 gm) was added and stirred for period of about 60 minutes, filtered the residual carbon through hyflo bed. The filtrate was added into aqueous sodium carbonate solution (100 ml), stirred for period of about 30 minutes at temperature of about 20° C. to about 30° C., filtered, washed with water and dried under reduced pressure at temperature of about 55° C. to about 60° C. to get Vericiguat. (1.0 gm); HPLC purity 99.7%

Example 24: Preparation of Vericiguat

Vericiguat hydrochloride (1.5 gm) was dissolved in methanol (10.5 mL) at temperature of about 20° C. to about 30° C. Activated carbon (0.6 gm) was added and stirred for period of about 60 minutes, filtered the residual carbon through hyflo bed. The filtrate was added into aqueous sodium carbonate solution (3.5% w/v sodium carbonate solution 15 ml), stirred for period of about 30 minutes at temperature of about 20° C. to about 30° C., filtered, washed with water and dried under reduced pressure at temperature of about 55° C. to about 60° C. to get Vericiguat. (1.0 gm); HPLC purity 99.7

Example 25 Preparation of Crystalline Vericiguat Form V1

Vericiguat (2.37 g obtained in from Example 1, Step 1) was dissolved in dimethyl sulphoxide (60 g) at room temperature and a solution was formed. The obtained solution was mechanically filtered (0.2 micron). The obtained clear yellow solution was lyophilized upon −45° C. to −30° C. to obtain Vericiguat Form V1.

The invention claimed is:

1. A crystalline Form VT1 of Vericiguat characterized by one or more of the following data:

a) an XRPD pattern having peaks at 6.0, 10.3, 15.6, 18.4 and 20.1 degrees 2-theta±0.2 degrees 2-theta;

b) a solid state $^{13}C$ NMR spectrum having peaks at 45.0, 51.3, 114.7, 120.2, 125.9, 139.8 and 160.5 ppm±0.2 ppm; or c) a solid state $^{13}C$ NMR spectrum having the following chemical shift absolute differences from a reference peak at 146.9 ppm±2 ppm of 101.9, 95.6, 32.2, 26.7, 21.0, 7.1 and 13.7 ppm±0.1 ppm.

2. The crystalline Form VT1 of Vericiguat according to claim 1, which is characterized by an XRPD pattern having peaks at 6.0, 10.3, 15.6, 18.4 and 20.1 degrees 2-theta±0.2 degrees 2-theta, and also having one, two, or three additional peaks selected from 12.4, 17.0 and 31.1 degrees two theta±0.2 degrees two theta.

3. The crystalline Form VT1 of Vericiguat according to claim 1, which is characterized by an XRPD pattern having peaks at 6.0, 10.3, 12.4, 15.6, 17.0 18.4, 20.1 and 31.1 degrees 2-theta±0.2 degrees 2-theta.

4. The crystalline Form VT1 of Vericiguat according to claim 1, which is further characterized by an XRPD pattern having an additional peak at 2.3±0.2 degrees 2-theta.

5. The crystalline Form VT1 of Vericiguat according to claim 1, which is further characterized by an XRPD pattern having an absence of a peak at 3.2±0.2 degrees 2-theta, or 5.1±0.2 degrees 2-theta, or 5.4±0.2 degrees 2-theta, or 6.4±0.2 degrees 2-theta, or 6.6±0.2 degrees 2-theta.

6. The crystalline Form VT1 of Vericiguat according to claim 1, wherein said crystalline form is an anhydrous form.

7. The crystalline Form VT1 of Vericiguat according to claim 1, which contains no more than about 20% of any other crystalline forms of Vericiguat.

8. The crystalline Form VT1 of Vericiguat according to claim 1, which contains no more than about 20% of amorphous Vericiguat.

9. A pharmaceutical composition comprising the crystalline form VT1 of Vericiguat according to claim 1.

10. A pharmaceutical formulation comprising the crystalline Form VT1 Vericiguat according to claim 1, with at least one pharmaceutically acceptable excipient.

11. A process for preparing a pharmaceutical formulation comprising combining the crystalline Form VT1 of Vericiguat according to claim 1 with at least one pharmaceutically acceptable excipient.

12. A medicament comprising the crystalline Form VT1 of Vericiguat according to claim 1.

13. A method of treating chronic heart failure, comprising administering a therapeutically effective amount of the crystalline Form VT1 of Vericiguat according to claim 1 to a subject in need of the treatment.

* * * * *